(12) United States Patent
Tsugo

(10) Patent No.: US 10,431,332 B2
(45) Date of Patent: Oct. 1, 2019

(54) MEDICAL ASSISTANCE DEVICE, OPERATION METHOD AND OPERATION PROGRAM FOR MEDICAL ASSISTANCE DEVICE, AND MEDICAL ASSISTANCE SYSTEM

(71) Applicant: FUJIFILM Corporation, Tokyo (JP)

(72) Inventor: Akinari Tsugo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1064 days.

(21) Appl. No.: 14/843,945

(22) Filed: Sep. 2, 2015

(65) Prior Publication Data
US 2016/0085928 A1  Mar. 24, 2016

(30) Foreign Application Priority Data
Sep. 24, 2014  (JP) .................... 2014-193296

(51) Int. Cl.
*G16H 15/00* (2018.01)
*G16H 50/20* (2018.01)

(52) U.S. Cl.
CPC ............. *G16H 15/00* (2018.01); *G16H 50/20* (2018.01); *Y02A 90/26* (2018.01)

(58) Field of Classification Search
CPC ........ G16H 15/20; G16H 50/20; G16H 15/00; Y02A 90/26
See application file for complete search history.

(56) References Cited

U.S. PATENT DOCUMENTS

| 2004/0059215 | A1 | 3/2004 | Nishimura et al. |
| 2010/0280847 | A1* | 11/2010 | Schaffer ............. G16H 50/20 705/3 |
| 2010/0332143 | A1* | 12/2010 | Onell ................. G01N 33/564 702/19 |

(Continued)

FOREIGN PATENT DOCUMENTS

| JP | 2003126045 | 5/2003 |
| JP | 2009032091 | 2/2009 |

(Continued)

OTHER PUBLICATIONS

"Office Action of Japan Counterpart Application," with machine English translation thereof, dated Jul. 26, 2017, p. 1-p. 10.

*Primary Examiner* — Christopher L Gilligan
(74) *Attorney, Agent, or Firm* — JCIPRNET

(57) ABSTRACT

There are provided a medical assistance device, an operation method of a medical assistance device, a non-transitory computer-readable recording medium, and a medical assistance system allowing a user to use a diagnostic assistance program with confidence. A comparison determination unit compares a designated data range, which is designated as a range to be used for input data of a diagnostic assistance program, with a recommended data range, which is set for each diagnostic assistance program and is recommended as a range to be used for input data. The comparison determination unit outputs information regarding surplus data, which is data outside the recommended data range in the designated data range, and information regarding missing data, which is data outside the designated data range in the recommended data range. A difference information output unit outputs the information of the surplus data or the missing data as difference information.

25 Claims, 25 Drawing Sheets

(56) References Cited

U.S. PATENT DOCUMENTS

| | | | | |
|---|---|---|---|---|
| 2012/0089893 | A1* | 4/2012 | Bousamra | A61B 5/14532 714/807 |
| 2012/0290324 | A1 | 11/2012 | Ribbing et al. | |
| 2012/0301864 | A1* | 11/2012 | Bagchi | G09B 7/02 434/362 |
| 2015/0193583 | A1* | 7/2015 | McNair | G16H 50/20 705/2 |

FOREIGN PATENT DOCUMENTS

| | | |
|---|---|---|
| JP | 2009-273558 | 11/2009 |
| JP | 2010142273 | 7/2010 |
| JP | 2013513845 | 4/2013 |

* cited by examiner

FIG. 8

| DISEASE (DISEASE ID) | DISPLAY ITEMS | | DIAGNOSTIC ASSISTANCE PROGRAM (PROGRAM ID) |
|---|---|---|---|
| DISEASE A (D1) | DOSING | DRUG A<br>DRUG B | DIAGNOSTIC ASSISTANCE PROGRAM (PR1)<br>DIAGNOSTIC ASSISTANCE PROGRAM (PR2)<br>DIAGNOSTIC ASSISTANCE PROGRAM (PR3)<br>DIAGNOSTIC ASSISTANCE PROGRAM (PR4)<br>⋮ |
| | VITAL SIGNS | BLOOD PRESSURE (TOP)<br>BLOOD PRESSURE (BOTTOM) | |
| | TEST SUBSTANCE EXAMINATIONS | BIOCHEMICAL TEST A<br>BIOCHEMICAL TEST B | |
| | IMAGE EXAMINATIONS | CT EXAMINATION | |
| DISEASE B (D2) | DOSING | DRUG A<br>DRUG C | DIAGNOSTIC ASSISTANCE PROGRAM (PR20)<br>DIAGNOSTIC ASSISTANCE PROGRAM (PR21)<br>⋮ |
| | VITAL SIGNS | BLOOD PRESSURE (TOP)<br>BLOOD PRESSURE (BOTTOM) | |
| | TEST SUBSTANCE EXAMINATIONS | BLOOD TEST E<br>BIOCHEMICAL TEST F | |
| | IMAGE EXAMINATIONS | ULTRASONIC EXAMINATION | |
| COMPLEX DISEASE AB (D1 + D2) | DOSING | DRUG A<br>DRUG B<br>DRUG C | DIAGNOSTIC ASSISTANCE PROGRAM (PR100)<br>⋮ |
| | VITAL SIGNS | BLOOD PRESSURE (TOP)<br>BLOOD PRESSURE (BOTTOM) | |
| | TEST SUBSTANCE EXAMINATIONS | BIOCHEMICAL TEST A<br>BIOCHEMICAL TEST B<br>BLOOD TEST E<br>BIOCHEMICAL TEST F<br>BIOCHEMICAL TEST G | |
| | IMAGE EXAMINATIONS | CT EXAMINATION<br>ULTRASONIC EXAMINATION | |

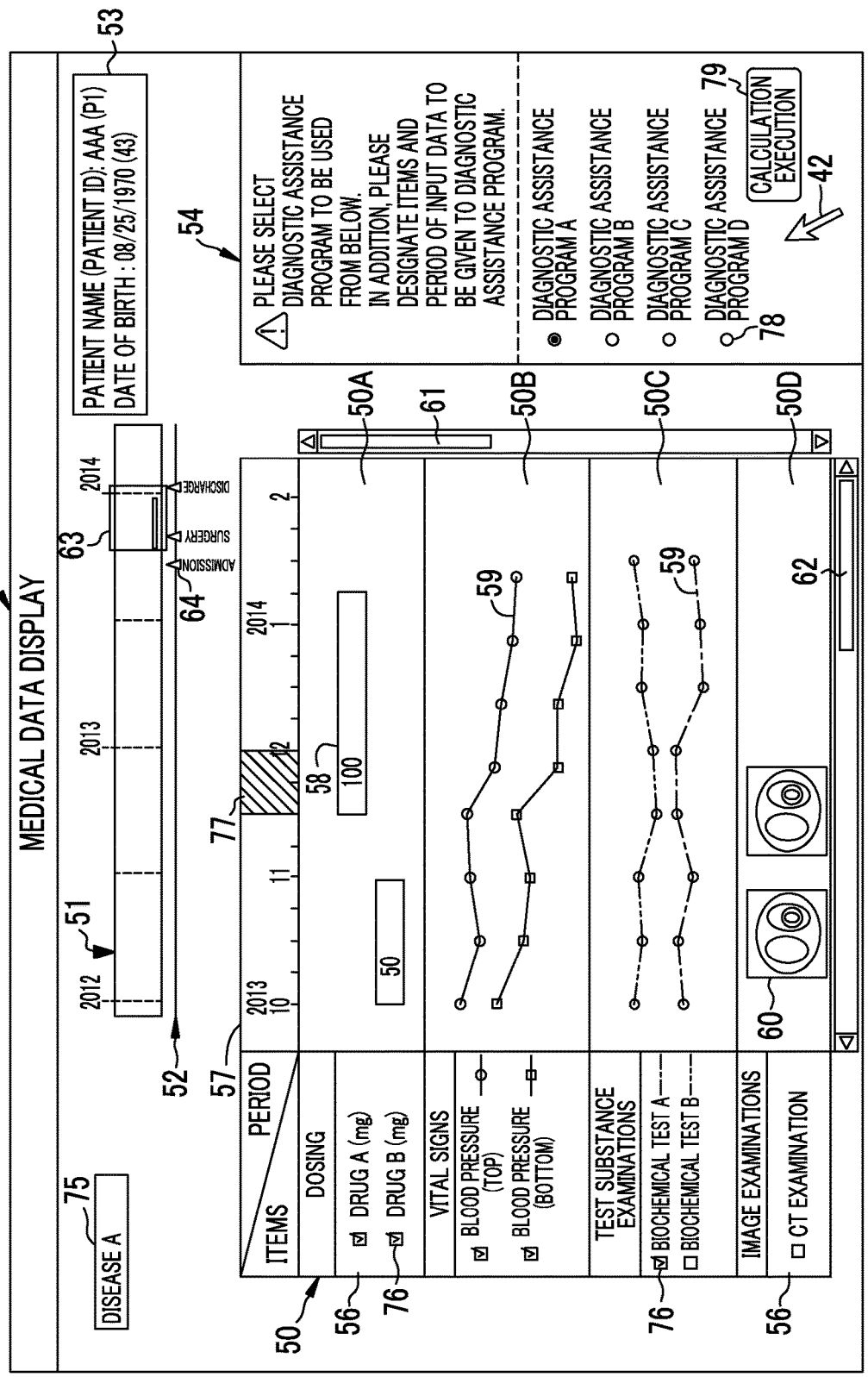

FIG. 11

| DIAGNOSTIC ASSISTANCE PROGRAM (PROGRAM ID) | RECOMMENDED DATA RANGE | | |
|---|---|---|---|
| | RECOMMENDED DATA ITEM | | RECOMMENDED DATA PERIOD |
| DIAGNOSTIC ASSISTANCE PROGRAM (PR1) | DOSING | DRUG A | ONE MONTH FROM DOSING DATE OF DRUG A |
| | VITAL SIGNS | BLOOD PRESSURE (TOP)   PULSE<br>BLOOD PRESSURE (BOTTOM)   BODY TEMPERATURE | |
| | TEST SUBSTANCE EXAMINATIONS | BIOCHEMICAL TEST A | |
| | IMAGE EXAMINATIONS | NONE | |
| DIAGNOSTIC ASSISTANCE PROGRAM (PR2) | DOSING | DRUG C | TEN DAYS FROM SURGERY DATE OF X SURGERY |
| | VITAL SIGNS | BLOOD PRESSURE (TOP)   PULSE<br>BLOOD PRESSURE (BOTTOM) | |
| | TEST SUBSTANCE EXAMINATIONS | BLOOD TEST E | |
| | IMAGE EXAMINATIONS | ULTRASONIC EXAMINATION | |

DIAGNOSTIC ASSISTANCE INFORMATION AND DIFFERENCE INFORMATION DISPLAY

DIAGNOSTIC ASSISTANCE INFORMATION:
· EXAMINATION VALUE OF BIOCHEMICAL TEST A EXCEEDS STANDARD VALUE. THIS IS THOUGHT TO BE SIDE EFFECTS OF DRUG A.

· RECOMMEND USE OF DRUG C
SIDE EFFECTS OF DRUG C ARE ...

⚠ SURPLUS DATA BELOW HAS NOT BEEN USED IN CALCULATION. IN ADDITION, THERE IS MISSING DATA. PLEASE CHECK.

· SURPLUS DATA
DRUG B
BLOOD TEST E

· MISSING DATA
PULSE
CT EXAMINATION
DATA OF TWO TO FOUR WEEKS FROM DOSING DATE OF DRUG A

↙ 42

CONFIRM — 126

| ITEM | | DEFAULT DATA |
|---|---|---|
| DOSING | DRUG A | 100 mg ONE MONTH |
| | DRUG B | 50 mg ONE MONTH |
| | ⋮ | ⋮ |
| VITAL SIGNS | BLOOD PRESSURE (TOP) | 125 mmHg |
| | BLOOD PRESSURE (BOTTOM) | 80 mmHg |
| | BODY TEMPERATURE | 36.5°C |
| | PULSE | 70 TIMES/MINUTE |
| | ⋮ | ⋮ |
| TEST SUBSTANCE EXAMINATIONS | BIOCHEMICAL TEST A | 20 IU/l |
| | BIOCHEMICAL TEST B | 15 IU/l |
| | ⋮ | ⋮ |

MEDICAL ASSISTANCE DEVICE, OPERATION METHOD AND OPERATION PROGRAM FOR MEDICAL ASSISTANCE DEVICE, AND MEDICAL ASSISTANCE SYSTEM

CROSS-REFERENCE TO RELATED APPLICATIONS

The present application claims priority under 35 U.S.C. § 119 to Japanese Patent Application No. 2014-193296, filed on Sep. 24, 2014. Each of the above application(s) is hereby expressly incorporated by reference, in its entirety, into the present application.

BACKGROUND OF THE INVENTION

1. Field of the Invention

The present invention relates to a medical assistance device, an operation method of a medical assistance device, a non-transitory computer-readable recording medium, and a medical assistance system.

2. Description of the Related Art

In the medical field, a medical assistance device that generates a medical data display screen to display medical data, such as examination data or measurement data acquired in the course of treatment for a patient, is known. Among these medical assistance devices, there is a medical assistance device having a function of using a diagnostic assistance program in addition to a function of generating the medical data display screen. The diagnostic assistance program is executed to perform calculation using medical data as input data and output a result of the calculation as diagnostic assistance information to assist the diagnosis of a patient. It is expected that the diagnostic assistance program will be variously developed by the development companies according to the type of disease or the like in the future.

JP2009-273558A discloses a medical checkup assistance device using a medical checkup assistance program that performs calculation using the medical data of a plurality of items recorded in time series, such as a cholesterol level, a blood sugar level, blood pressure, the amount of smoking, and sleeping hours, as input data and outputs the risk of developing a disease as medical checkup assistance information. In the technique disclosed in JP2009-273558A, a user designates a period, which is to be used for input data, of the medical data in the entire course of treatment for the patient. Then, using the medical checkup assistance program, the risk of developing the disease is calculated based on the medical data of the period designated by the user.

SUMMARY OF THE INVENTION

Incidentally, each diagnostic assistance program is created for each purpose of diagnostic assistance, such as the analysis of a specific disease. Therefore, a recommended data range that is recommended for the range of medical data to be used for input data should be set in advance. Specifically, there are two types of the range of medical data; that is, a range of an item determined by the designation of an item in the medical data of a plurality of items and a period determined by the designation of a temporal range in the medical data in the entire course of treatment for the patient.

On the other hand, since the content of diagnostic assistance information may change depending on the range to be used for input data, a user himself or herself may want to designate a range to be used for input data. Specifically, this is a case in which the user wants to designate the items of specific medical data in which the user is interested or a case in which the user wants to designate a period of medical data to be used for the execution of a diagnostic assistance program as disclosed in JP2009-273558A.

In such an environment of use of a diagnostic assistance program, the user may not be aware of the recommended data range. Accordingly, the range designated by the user (hereinafter, referred to as a designated data range) may be different from the recommended data range. In particular, the advances of medical research or the innovation of medical technology in recent years, such as development of new drugs or establishment of new knowledge, is remarkable. Moreover, with the development of information technology, also in the medical field, a large amount of various kinds of information have been collected. In other words, the accumulation of so-called big data is in progress. In order to adapt to such a trend, it is expected that many kinds of diagnostic assistance programs will be developed day by day and be obsolete quickly. In such a situation in which there are many types of diagnostic assistance programs and the obsolescence is quick, it is unreasonable for the user to remember the recommended data range for each type of diagnostic assistance program. Accordingly, a possibility that the designated data range will become different from the recommended data range is expected to increase gradually.

Hereinafter, in the recommended data range, an item of medical data that is recommended is referred to as a recommended data item, and a period of medical data that is recommended is referred to as a recommended data period. In addition, in the designated data range, an item of medical data that is designated by the user is referred to as a designated data item, and a period of medical data that is designated by the user is referred to as a designated data period.

As a case in which there is a difference between the designated data range and the recommended data range, there is a case in which medical data outside the recommended data range is included in the designated data range. For example, a case in which a surplus item other than recommended data items is included in designated data items or a case in which the designated data period extends off the recommended data period can be considered. In this case, for example, a diagnostic assistance program is executed without using the medical data of the surplus item other than the recommended data items as input data or without using the medical data in a period other than the recommended data period as input data, thereby outputting the diagnostic assistance information. Then, since the user cannot see that the calculation has been performed without using the items or the period designated by the user, there is a possibility that the user will perform diagnosis by mistakenly believing that the items or the period designated by himself or herself has been used for the output of diagnostic assistance information.

In addition, as a case in which there is a difference between the designated data range and the recommended data range, there is a case in which medical data outside the designated data range is included in the recommended data range. For example, a case in which the number of designated data items is smaller than the number of recommended data items or a case in which the designated data period is shorter than the recommended data period can be considered. In this case, the diagnostic assistance program is executed by using, for example, medical data of the limited designated data range, which is narrower than the recommended data range, as input data, thereby outputting the diagnostic assistance information. Thus, even though there is input data that is missing compared with the recommended data range and should be included in the calculation, the diagnostic assistance information is output without using the input data. Accordingly, the reliability of the diagnostic assistance information is not guaranteed. However, since the user does not know such a situation, there is a possibility that the user will perform diagnosis by mistakenly believing that the diagnostic assistance information is reliable.

Thus, there has been a problem that the user cannot use a diagnostic assistance program with confidence in a situation in which there is no choice but to perform diagnosis without knowing the reliability of the diagnostic assistance information output by the execution of the diagnostic assistance program.

It is an object of the invention to provide a medical assistance device allowing a user to use a diagnostic assistance program with confidence, an operation method of a medical assistance device, a non-transitory computer-readable recording medium, and a medical assistance system.

In order to solve the aforementioned problem, a medical assistance device of the invention includes: a program control unit that controls a diagnostic assistance program that is executed to perform calculation using medical data of a patient as input data and output a result of the calculation as diagnostic assistance information for assisting diagnosis of the patient; a designated data range receiving unit that receives an input of a designated data range, which is designated as a range to be used for the input data, of the medical data; a recommended data range acquisition unit that acquires a recommended data range that is set for each diagnostic assistance program and is recommended as a range to be used for the input data; and a difference information output unit that, in a case where there is a difference between the designated data range and the recommended data range as a result of comparison between the designated data range received by the designated data range receiving unit and the recommended data range acquired by the recommended data range acquisition unit, outputs difference information indicating the difference.

As examples of the difference information, there is difference information indicating the content of the specific difference between the designated data range and the recommended data range and difference information that simply indicates that there is a difference between the designated data range and the recommended data range.

It is preferable that in a case where surplus data that is data outside the recommended data range and inside the designated data range is present, the difference information output unit outputs the surplus data as the difference information. In this case, it is preferable that the program control unit executes the diagnostic assistance program using only the medical data of the recommended data range as the input data in a case where there is the surplus data.

It is preferable that in a case where missing data that is data outside the designated data range and inside the recommended data range is present, the difference information output unit outputs information regarding the missing data as the difference information. In addition, it is preferable that the program control unit executes the diagnostic assistance program using only the medical data of the designated data range as the input data in a case where there is the missing data.

It is preferable that the medical assistance device further includes a supplementary data output unit that outputs supplementary data to supplement the missing data. In this case, it is preferable that the program control unit executes the diagnostic assistance program using data, which is obtained by adding the supplementary data to the medical data of the designated data range, as the input data. The difference information output unit may output the supplementary data as the difference information.

For example, the supplementary data is default data that is set in advance and is applicable in common to a plurality of the patients. Alternatively, the supplementary data may be estimated data that is estimated for each patient based on the medical data.

For example, the medical data includes a plurality of items, and at least one of the plurality of items is recorded in time series, and the designated data range is at least one of a range of the item determined by designation of the item and a period determined by designation of a temporal range.

It is preferable that the medical assistance device further includes a screen generation unit that generates a medical data display screen to display the medical data. In this case, it is preferable that the medical data display screen has a function of designating the designated data range, and the designated data range receiving unit receives the designated data range that is designated through the medical data display screen.

The difference information may be displayed on the medical data display screen. In addition, the diagnostic assistance information may be displayed on the medical data display screen. In addition, it is preferable that the medical data display screen is a screen that is common to a plurality of diagnostic assistance programs.

It is preferable the diagnostic assistance program used for each medical unit is registered in advance, and the program control unit executes the diagnostic assistance program corresponding to the medical unit. For example, the medical unit is at least one of the patient, a disease which the patient suffers from, a department, a medical facility, an event that occurs in a course of treatment for the patient, a medical phase that is a progressive stage of treatment or disease, and a medical purpose.

An operation method of a medical assistance device of the invention includes: a program control step of controlling a diagnostic assistance program that is executed to perform calculation using medical data of a patient as input data and output a result of the calculation as diagnostic assistance information for assisting diagnosis of the patient; a designated data range reception step of receiving an input of a designated data range, which is designated as a range to be used for the input data, of the medical data; a recommended data range acquisition step of acquiring a recommended data range that is set for each diagnostic assistance program and is recommended as a range to be used for the input data; and a difference information output step of, in a case where there is a difference between the designated data range and the recommended data range as a result of comparison between the designated data range received in the designated data range reception step and the recommended data range acquired in the recommended data range acquisition step, outputting difference information indicating the difference, in which all of the steps are performed using the medical assistance device described above.

There is provided a non-transitory computer-readable recording medium on which an operation program for a medical assistance device of the invention is recorded. The program causes a computer to execute: a program control function of controlling a diagnostic assistance program that is executed to perform calculation using medical data of a patient as input data and output a result of the calculation as diagnostic assistance information for assisting diagnosis of the patient; a designated data range reception function of receiving an input of a designated data range, which is designated as a range to be used for the input data, of the medical data; a recommended data range acquisition function of acquiring a recommended data range that is set for each diagnostic assistance program and is recommended as a range to be used for the input data; and a difference information output function of, in a case where there is a difference between the designated data range and the recommended data range as a result of comparison between the designated data range received through the designated data range reception function and the recommended data range acquired through the recommended data range acquisition step, outputting difference information indicating the difference, and all of the functions are realized using the medical assistance device described above.

In addition, a medical assistance system of the invention includes: a medical assistance server; a client terminal; a network that communicably connects the medical assistance server and the client terminal to each other; and the medical assistance device described above.

It is preferable that the medical assistance system further includes: a supplementary data output unit that, in a case where missing data that is data outside the designated data range and inside the recommended data range is present, outputs supplementary data to supplement the missing data. In this case, it is preferable that the program control unit executes the diagnostic assistance program using data, which is obtained by adding the supplementary data to the medical data of the designated data range, as the input data.

It is preferable that the program control unit, the difference information output unit, and the supplementary data output unit are provided in the medical assistance server. Alternatively, the program control unit and the difference information output unit may be provided in the medical assistance server, and the supplementary data output unit may be provided in the client terminal, and the medical assistance server may transmit information regarding the missing data to the client terminal, and the client terminal may transmit the supplementary data to the medical assistance server.

The recommended data range acquisition unit is provided in the medical assistance server, and reads the recommended data range from a storage unit that stores the recommended data range. Alternatively, the recommended data range acquisition unit is provided in the client terminal, and receives the recommended data range that is transmitted from a storage unit of the medical assistance server that stores the recommended data range.

According to the invention, the difference information indicating that there is a difference between the designated data range and the recommended data range is output. Accordingly, when the user's designation of a range is wrong, the user can see the situation. In addition, the user can see whether or not the diagnostic assistance information is reliable. Therefore, it is possible to provide a medical assistance device allowing a user to use a diagnostic assistance program with confidence, an operation method of a medical assistance device, a non-transitory computer-readable recording medium, and a medical assistance system.

BRIEF DESCRIPTION OF THE DRAWINGS

FIG. 8 is a diagram showing the content of a disease-specific list.
FIG. 9 is a diagram showing a state in which an item and a period have been designated on the medical data display screen.
FIG. 11 is a diagram showing the content of a recommended data range list.
FIG. 19 is a diagram showing a diagnostic assistance information and difference information display screen.
FIG. 21 is a diagram showing the content of a default data list.

DESCRIPTION OF THE PREFERRED EMBODIMENTS

First Embodiment

Figure 1:
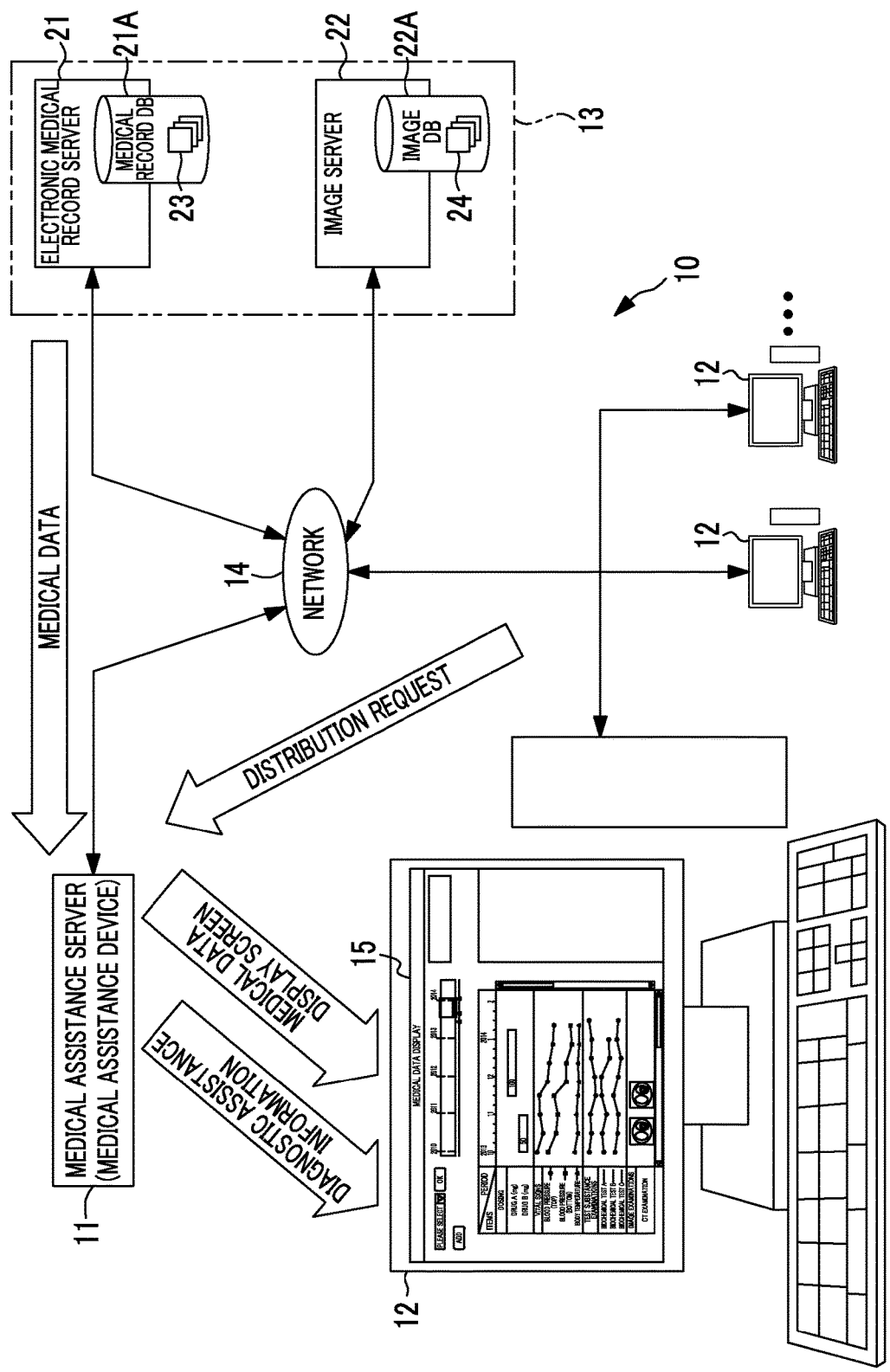
FIG. 1 is an explanatory diagram showing a medical assistance system.

In FIG. 1, a medical assistance system 10 is a computer system for managing and using medical information in a medical facility, such as a hospital. The medical assistance system 10 includes a medical assistance server 11, a client terminal 12, and a server group 13. These are communicably connected to each other through a network 14, such as a local area network (LAN) provided in the medical facility.

The medical assistance server 11 functions as a medical assistance device of the invention. Specifically, the medical assistance server 11 receives a distribution request from the client terminal 12. In response to the received distribution request, the medical assistance server 11 transmits a request for acquisition of medical data, which has been acquired in the entire course of treatment for the patient, to the server group 13. The medical assistance server 11 acquires the medical data transmitted from the server group 13 in response to the acquisition request, and generates a medical data display screen 15 (refer to FIG. 6 or the like) based on the acquired medical data. The medical assistance server 11 transmits the generated medical data display screen 15 to the client terminal 12 that has made the distribution request.

In addition, the medical assistance server 11 has a function of using a plurality of diagnostic assistance programs 101 (refer to FIG. 15), and outputs diagnostic assistance information that is calculated by executing the diagnostic assistance programs 101 using the medical data as input data. The diagnostic assistance information is transmitted to the client terminal 12 by being superimposed on the medical data display screen 15 (refer to FIG. 10).

The client terminal 12 is installed in each department, such as internal medicine, surgery, otolaryngology, and ophthalmology, in the medical facility, and is operated by the doctor in each department that is a user. The client terminal 12 transmits a distribution request for medical data to the server group 13, and transmits a distribution request for the medical data display screen 15 to the medical assistance server 11. The client terminal 12 displays the medical data or the medical data display screen 15, which is transmitted from the server group 13 or the medical assistance server 11 in response to the distribution request, so that the doctor can see it. That is, the client terminal 12 functions as a viewer terminal for a doctor to view the medical data or the medical data display screen 15.

The medical assistance server 11 distributes the medical data display screen 15 to the client terminal 12, for example, in the form of XML data for web distribution created by a markup language, such as Extensible Markup Language (XML). The client terminal 12 reproduces and displays the medical data display screen 15 on the web browser based on the XML data.

The server group 13 searches for medical data corresponding to the distribution request from the client terminal 12, and transmits the searched medical data to the client terminal 12. In addition, the server group 13 searches for medical data corresponding to the acquisition request from the medical assistance server 11, and transmits the searched medical data to the medical assistance server 11.

The server group 13 includes an electronic medical record server 21 and an image server 22. The electronic medical record server 21 includes a medical record database (hereinafter, abbreviated as a DataBase (DB)) 21A in which an electronic medical record 23 is stored. In the electronic medical record 23, medical examination records data such as the content of interview or the diagnostic content, examination data such as examination values of medical examinations including test substance examinations (for example, a blood test and a biochemical test) and physiological tests (for example, electroencephalography), measurement data such as measurement values of vital signs (for example, patient's heart rate, pulse, blood pressure, and body temperature), and treatment records data such as treatment, surgery, and dosing are input as medical data. These various kinds of data of the electronic medical record 23 can be input to the client terminal 12, and the electronic medical record 23 can be viewed at the client terminal 12.

The image server 22 is a so-called picture archiving and communication system (PACS) server, and has an image DB 22A in which an examination image 24 is stored. The examination image 24 is an image obtained by various image examinations, such as a computed tomography (CT) examination, a magnetic resonance imaging (MRI) examination, a simple X-ray examination, an ultrasonic examination, and an endoscopic examination. For example, the examination image 24 is created in the data file format of digital imaging and communications in medicine (DICOM) standards. The examination image 24 can be viewed at the client terminal 12.

Figure 2:
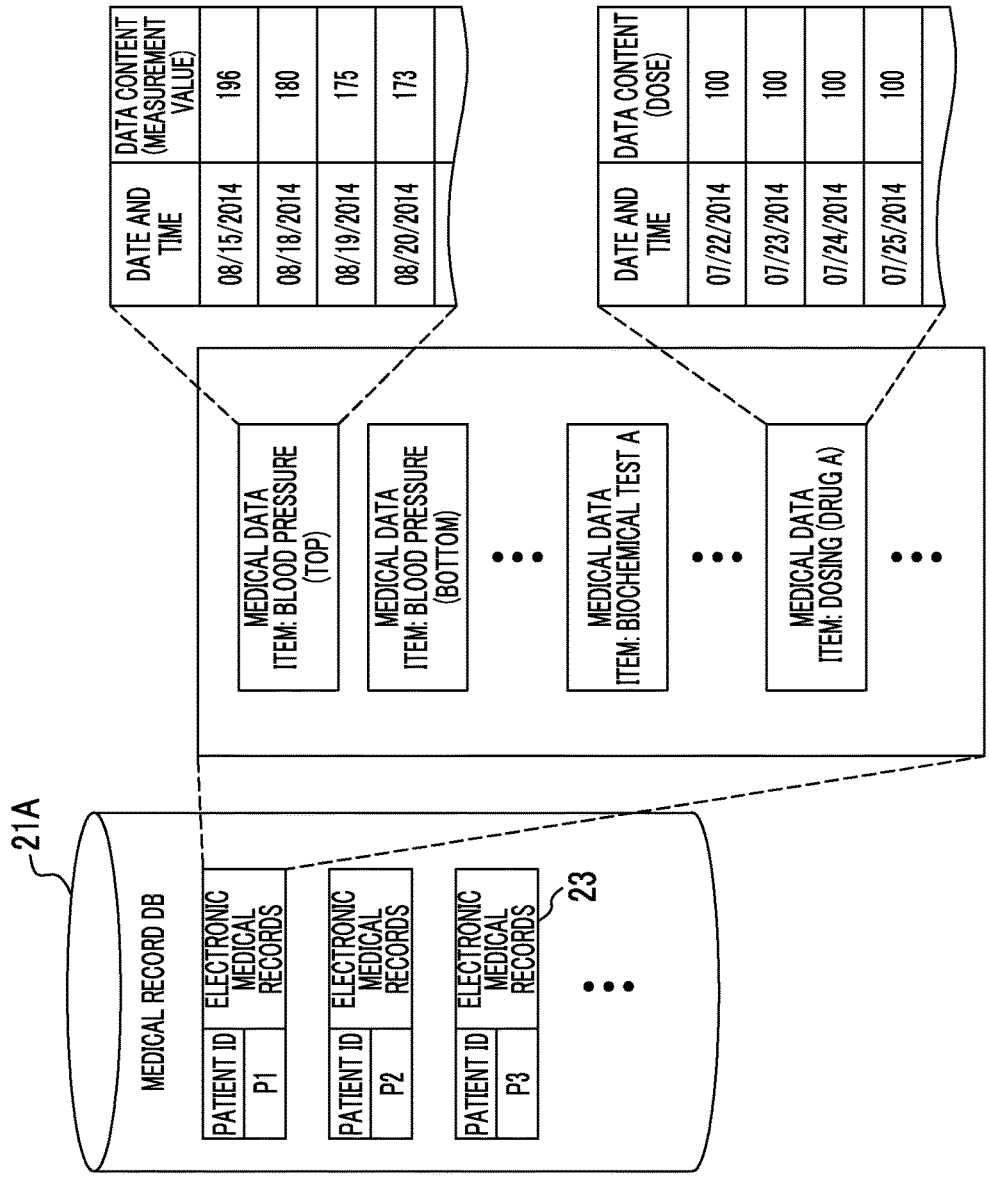
FIG. 2 is a diagram showing the content of electronic medical records stored in a medical record DB.
Figure 3:
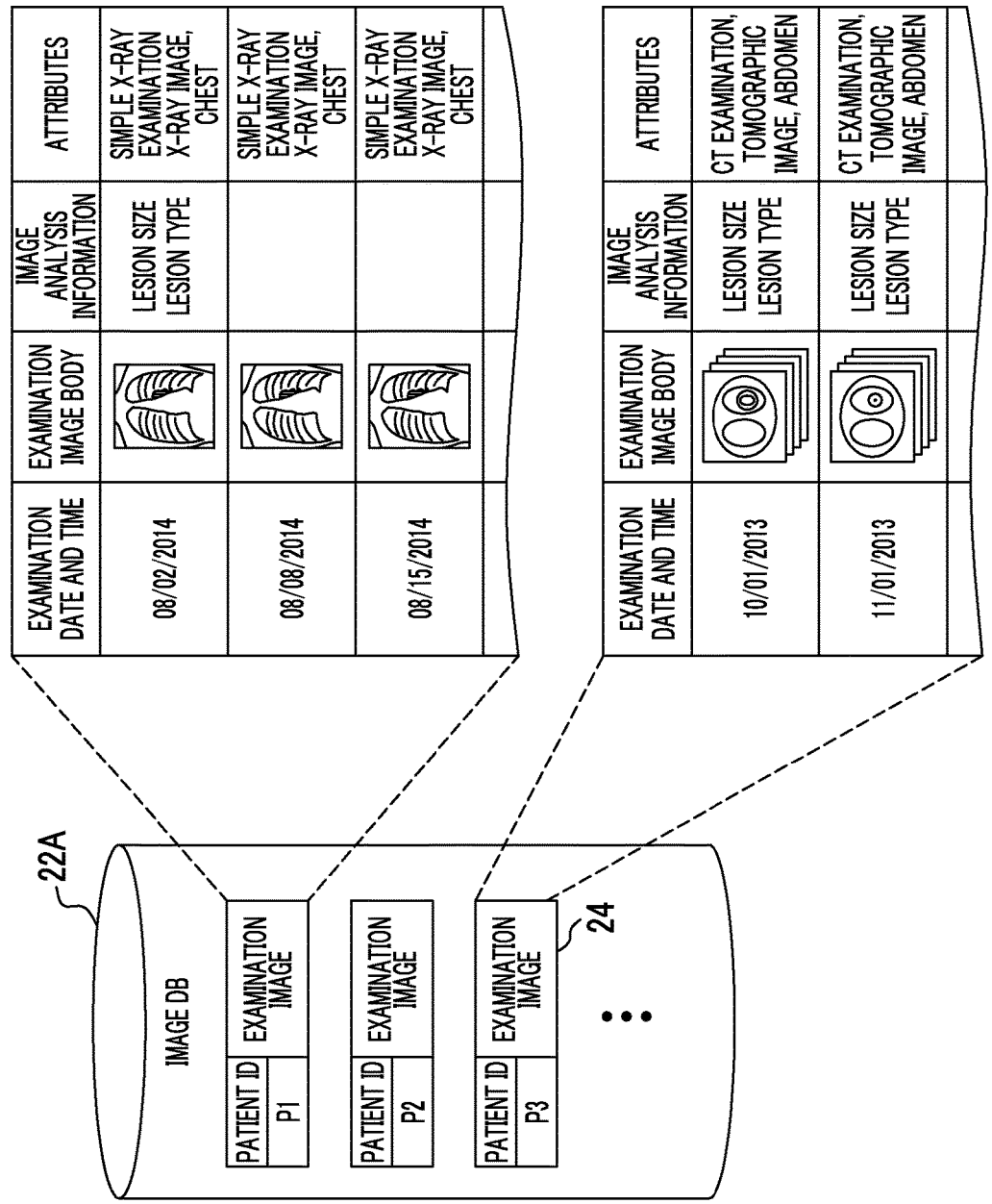
FIG. 3 is a diagram showing the content of an examination image stored in an image DB.

In the electronic medical record 23 and the examination image 24, patient identification data (ID) that is a number for identifying an individual patient or the like is stored as supplementary information so as to be associated therewith (refer to FIGS. 2 and 3). In the electronic medical record 23 and the examination image 24, searching from the DB 21A and DB 22A can be performed by using the supplementary information, such as a patient ID, as a search keyword.

In addition to the servers 21 and 22, the server group 13 may also include various servers, such as a health management information server for handling health management information that the patient measures daily using a blood pressure measuring instrument, a weighing scale, or the like at home and a genetic test information server for handling genetic test information that is a result of a genetic test of a patient. In recent years, it has become possible to mail a genetic test kit and a test result to patients. Therefore, since the patients themselves can easily perform genetic tests at home, it is expected that the genetic test will be more widespread in the future.

In FIG. 2, the electronic medical record 23 stored in the medical record DB 21A is managed in units of a patient by being associated with patient IDs, such as P1, P2, P3, . . . . Not only the patient ID but also the basic information (not shown) of the patient, such as the patient's name, sex, date of birth or age, address, and telephone number, and medical data of a plurality of items are recorded in the electronic medical record 23. Medical data is arranged in items, such as "blood pressure (top)", "blood pressure (bottom)", "biochemical test A", and "dosing (drug A)", and is recorded in time series. Although not shown in FIG. 2, the medical data includes not only the above-described medical examination records data such as the content of interview or the diagnostic content, measurement values of vital signs (for example, a heart rate, a pulse, and body temperature other than the blood pressure), and dosing but also treatment records data such as treatment or surgery. When there is a health management information server or a genetic test information server, health management information or genetic test information that is obtained from these servers and is recorded in the electronic medical record 23 is also included in the medical data.

The record of one case of each item of medical data includes information regarding the date and time, such as visit date and time, examination date and time, measurement date and time, and dosing date and time (date and time when medication was performed or prescription date and time), and the data content, such as the content of interview, the diagnostic content, examination values, measurement values, and dose. When the item is dosing, it may take time until the dosing effect appears. Accordingly, dosing (taking drugs) over a predetermined period of time may be instructed by one prescription, for example, "take a predetermined amount per day continuously for 5 days". In this case, date and time for which the taking of the medicine is scheduled is recorded as the dosing date and time.

In FIG. 3, the examination image 24 stored in the image DB 22A is managed in units of a patient by being associated with a patient ID, similar to the electronic medical record 23. Not only the patient ID but also the attributes of each examination image, such as examination date and time when an image examination was performed, image analysis information, type of image examination (for example, "X-ray examination" or "CT examination"), type of each examination image ("X-ray image" or "tomographic image"), and an imaging part (for example, "chest" or "abdomen"), are associated with the examination image 24, as supplementary information. The type of image examination is used as an item of medical data. The image server 22 transmits the examination image 24 to the medical assistance server 11 or the client terminal 12, as medical data, together with the supplementary information, such as the image analysis information or the attributes.

In a simple X-ray examination, one X-ray image is captured by one image examination in many cases. However, as a tomographic image acquired by the CT examination, a plurality of examination images 24 may be captured by one image examination. Thus, when a plurality of examination images 24 are captured by one image examination, a common ID is assigned to each examination image 24 in order to indicate that the plurality of examination images 24 have been obtained by one image examination, and the plurality of examination images 24 are collectively managed as one examination image 24. This is the same for a case in which a plurality of examination images 24 are captured by a simple X-ray examination.

The image analysis information is information regarding the size, type, and the like of a lesion in the examination image 24. When the image examination is an ultrasonic examination, a blood flow measurement value obtained by analyzing the ultrasonic image is also included in the image analysis information. The image analysis information is a kind of diagnostic assistance information obtained by the image analysis using the diagnostic assistance program 101, for example. Alternatively, a result obtained when a doctor reads and determines the examination image 24 in the client terminal 12 may be input as the image analysis information.

The medical assistance server 11, the client terminal 12, and the servers 21 and 22 of the server group 13 are formed by installing a control program, such as an operating system, or an application program, such as a server program or a client program, into a computer as a base, such as a server computer, a personal computer, or a workstation.

Figure 4:
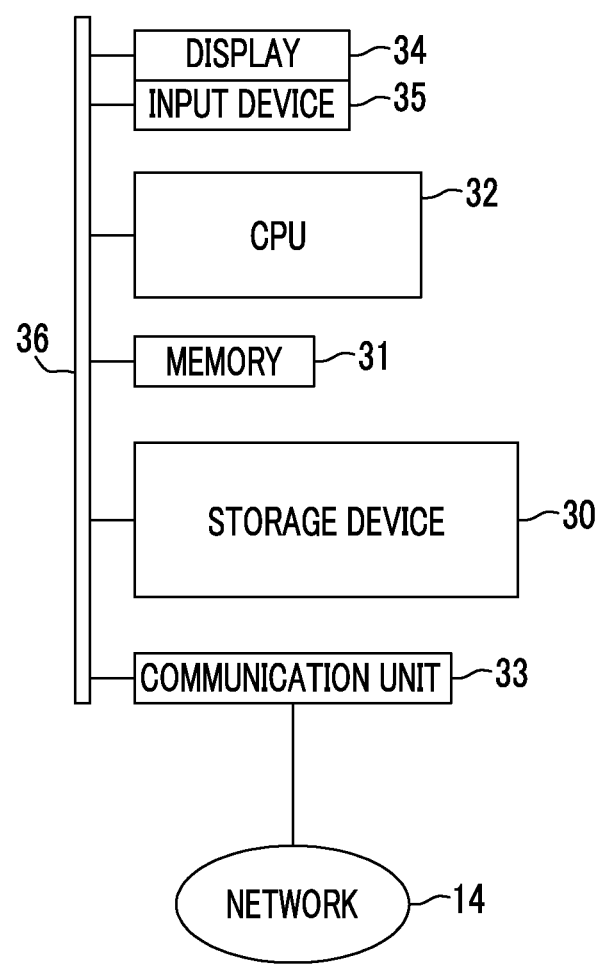
FIG. 4 is a block diagram showing the configuration of a computer that forms a medical assistance server or a client terminal.

In FIG. 4, the basic configurations of computers that configure the medical assistance server 11, the client terminal 12, and the like are the same, and each computer includes a storage device 30, a memory 31, a central processing unit (CPU) 32, a communication unit 33, a display 34, and an input device 35. These are connected to each other through a data bus 36.

The storage device 30 is a hard disk drive, which is built in a computer that forms the medical assistance server 11 or the client terminal 12 or which is connected to the computer through a cable or a network, or a disk array formed by connecting a plurality of hard disk drives. A control program such as an operating system, various application programs, and display data of various operation screens associated with these programs are stored in the storage device 30.

The memory 31 is a work memory required when the CPU 32 executes processing. The CPU 32 performs overall control of each unit of the computer by loading a program stored in the storage device 30 to the memory 31 and executing the processing according to the program.

The communication unit 33 is a network interface to perform transmission control of various kinds of information through the network 14. The display 34 displays various operation screens corresponding to the operation of the input device 35, such as a mouse or a keyboard. The operation screen has an operation function based on the graphical user interface (GUI). Each computer that forms the medical assistance server 11 or the client terminal 12 receives an input of an operation instruction from the input device 35 through the operation screen. In the following explanation, for the sake of distinction, a suffix "A" is attached to the reference numeral of each unit of the computer that forms the medical assistance server 11, and a suffix "B" is attached to the reference numeral of each unit of the computer that forms the client terminal 12.

An application program, such as electronic medical record software for viewing or editing the electronic medical record 23, image viewing software for viewing the examination image 24, or viewer software for viewing the medical data display screen 15, is installed in the client terminal 12.

Figure 5:
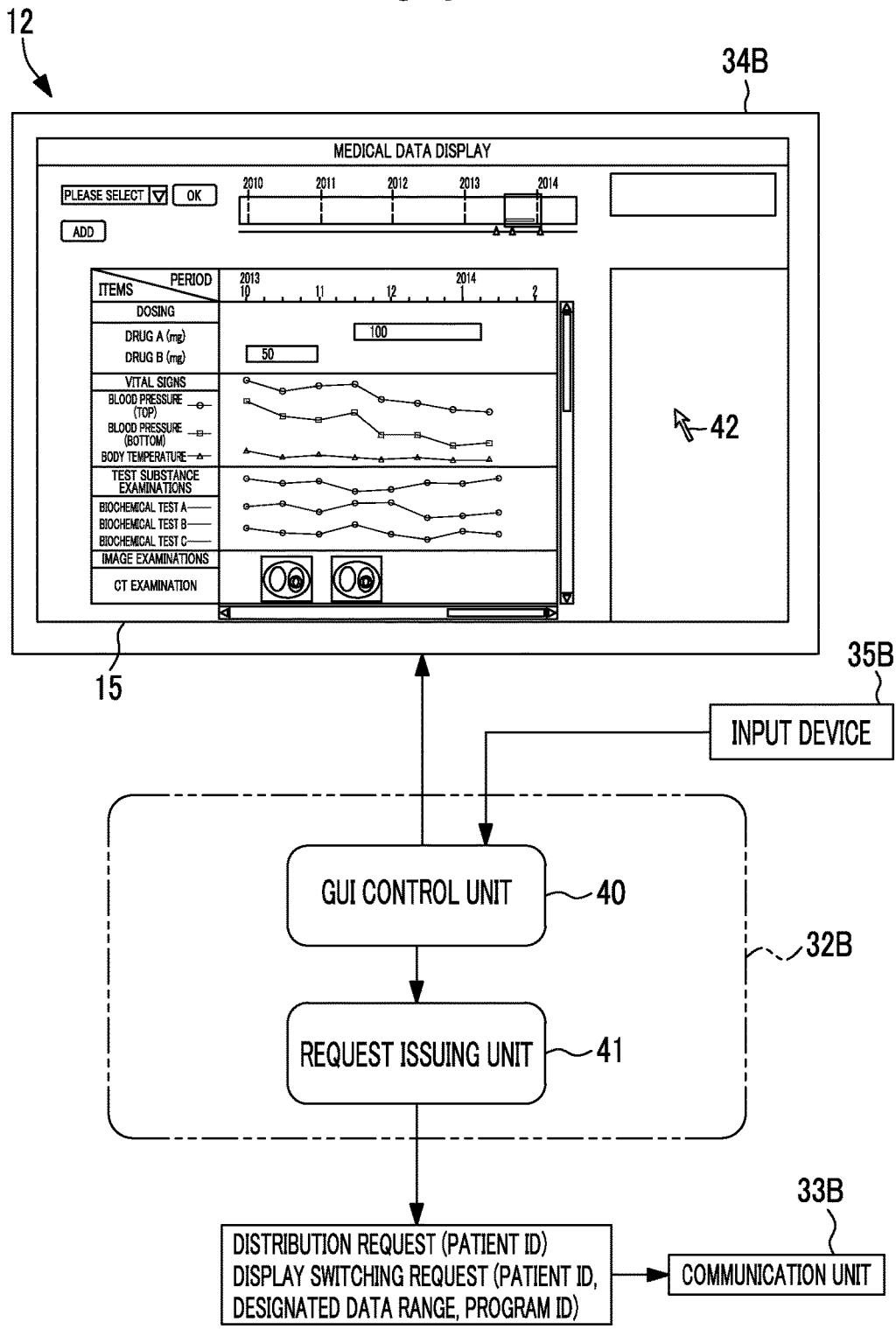
FIG. 5 is a block diagram showing a client terminal.

In FIG. 5, when the viewer software of the medical data display screen 15 is started, the CPU 32B of the client terminal 12 cooperates with the memory 31B to function as a GUI control unit 40 and a request issuing unit 41. The GUI control unit 40 displays the medical data display screen 15 transmitted from the medical assistance server 11 on the web browser of the display 34B. The GUI control unit 40 performs screen control according to an operation instruction that is input from the input device 35B through the medical data display screen 15, such as a button clicking operation using a cursor 42.

The request issuing unit 41 issues various requests to the medical assistance server 11, according to the operation instruction of the input device 35B given through the GUI control unit 40, to the communication unit 33B. The various requests include a distribution request for the medical data display screen 15 and a display switching request for the medical data display screen 15. The distribution request includes a patient ID. The patient ID is input through the startup screen of the viewer software, for example.

The display switching request is a process of requesting the medical assistance server 11 to switch the display content of the medical data display screen 15 according to the display switching instruction of the medical data display screen 15 using the input device 35B. There are two types of display switching requests. One includes a disease ID corresponding to the selection of a disease, and the other includes a designated data range, which is designated by the doctor as a range to be used for the input data of the diagnostic assistance program 101, and a program ID of the diagnostic assistance program 101 that is selected by the doctor as a program to be used.

The disease ID is a number for identifying each disease, such as lung cancer or a gastric ulcer. The program ID is a number for identifying each diagnostic assistance program 101. The designated data range includes a designated data item, which is determined by the designation of each item of medical data, and a designated data time, which is determined by the designation of a temporal range, as will be described later.

Figure 6:
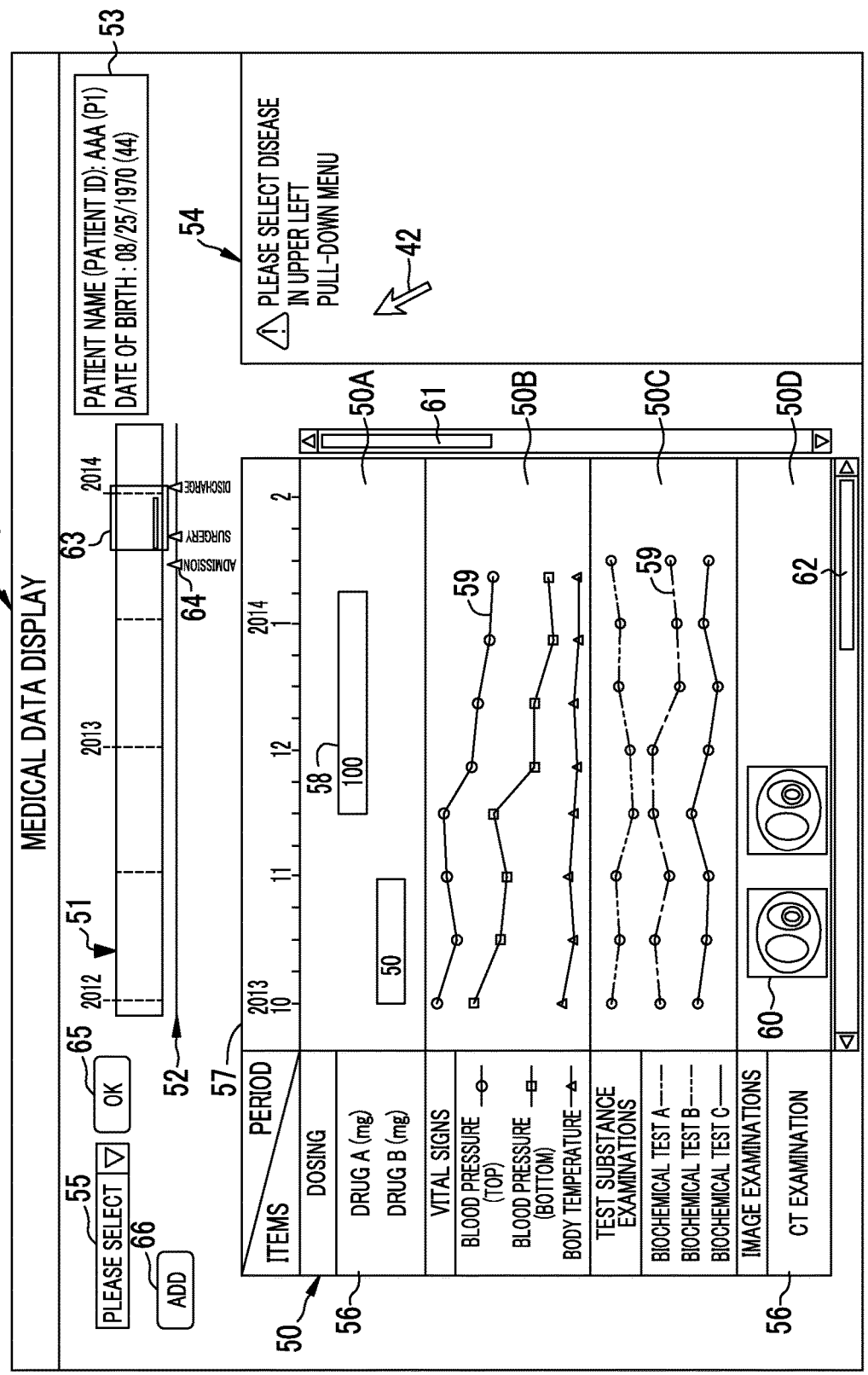
FIG. 6 is a diagram showing a medical data display screen.

In FIG. 6, the medical data display screen 15 includes a medical data display region 50, a period display region 51, an event display region 52, a patient information display region 53, a various information display region 54, and a pull-down menu 55.

In the medical data display region 50, the vertical axis indicates an item of medical data, and the horizontal axis indicates time. An item display column 56 is provided on the left, and a period display column 57 is provided on the top. In the item display column 56, major category names of items of medical data, such as "dosing", "vital signs", "test substance examinations", and "image examinations", and names of items such as "drug A, drug B", "blood pressure (top), blood pressure (bottom), body temperature", "biochemical test B, biochemical test B, biochemical test C", and "CT examination" are displayed. The period display column 57 shows a period for which medical data displayed in the medical data display region 50, of the medical data in the entire course of treatment for the patient, has been acquired (hereinafter, referred to as a first period). In the period display column 57, markings and information, such as year, month, and day, are arranged according to the set time scale. In FIG. 6, the first period is approximately three and a half months from October, 2013 to mid-January, 2014.

The medical data display region 50 is divided into a plurality of sub-regions 50A, 50B, 50C, 50D, . . . in the vertical direction by a plurality of item display columns 56. Major category names of items of "dosing", "vital signs", "test substance examinations", and "image examinations" are assigned to the sub-regions 50A, 50B, 50C, and 50D, respectively. In the sub-region 50A, start and end dates of dosing in the first period and a bar 58 indicating a dose are displayed. The inside of the parentheses of the item display column 56 of "dosing" indicates a unit of the dose displayed on the bar 58. In the sub-regions 50B and 50C, a line graph 59 obtained by plotting the measured values of vital signs or the examination values of test substance examinations in the first period and connecting these values in lines is displayed. In the item display columns 56 of "vital signs" and "test substance examinations", the legend of the line graph 59 is displayed. In the sub-region 50D, a thumbnail image 60 of the examination image 24 obtained in the first period is displayed. The bar 58, the plot of measured values or examination values forming the line graph 59, and the thumbnail image 60 are disposed at positions corresponding to the dosing date and time, measurement date and time, and examination date and time.

The medical data display region 50 can be vertically and horizontally scrolled by scroll bars 61 and 62. By operating the scroll bar 61 for scrolling in the vertical direction, it is possible to change the display ranges of the item display column 56 and the sub-regions. In addition, by operating the scroll bar 62 for scrolling in the horizontal direction, it is possible to change the display range of the first period.

The period display region 51 is a region where a period with a relatively longer time scale (hereinafter, referred to as a second period) than the first period shown in the period display column 57 is displayed. In the period display region 51, information of the year and the scale of each year are displayed, and a period indicator 63 is provided. The period indicator 63 shows to which part of the second period the first period corresponds. The width of the period indicator 63 corresponds to the width of the first period in the time scale of the second period. Since the first period is approximately three and a half months in FIG. 6, the width of the period indicator 63 corresponds to the width of three and a half months in the time scale of the second period.

The period indicator 63 moves the period display region 51 in the horizontal direction in conjunction with the operation of the scroll bar 62. It is also possible to change the display range of the first period by moving the period indicator 63 itself in the horizontal direction or changing the width of the period indicator 63. The first period to be first displayed may be a period before a predetermined period from the acquisition of the latest medical data, or may be designated when a doctor inputs a patient ID on the startup screen.

The event display region 52 shows the date and time when the event in the course of treatment for the patient has occurred, such as admission and discharge dates or a surgery date, together with an arrow 64 for the event name and the period display region 51. Basic information, such as the patient name of a patient of a patient ID input on the startup screen of the viewer software, the patient ID, and the date of birth, is displayed in the patient information display region 53.

In the various information display region 54, various kinds of information to be communicated to the doctor are displayed. In the example shown in FIG. 6, a message prompting the selection of a disease in the pull-down menu 55 is displayed in the various information display region 54.

The pull-down menu 55 is a display for selecting a disease. In the pull-down menu 55, the names of all diseases, such as "disease A" and "disease B" (refer to FIG. 8), are displayed as options. An OK button 65 is provided next to the pull-down menu 55, and an add button 66 is provided below the pull-down menu 55. By clicking the add button 66 with the cursor 42, it is possible to newly add the pull-down menu 55. Therefore, it is possible to select a complex disease, such as a "complex disease AB" (refer to FIG. 8). Complex diseases are more common in the elderly. As aging becomes faster in recent years, the number of patients suffering from complex diseases is also increasing. For this reason, such a function is effective.

When a disease is selected by operating the pull-down menu 55 with the cursor 42 and the OK button 65 is clicked, a display switching request including the disease ID of the selected disease is transmitted from the client terminal 12 to the medical assistance server 11. It is possible to provide a search bar for searching for a candidate for the disease, which is predicted from the symptoms, with the symptoms of the patient as a search keyword.

Figure 7:
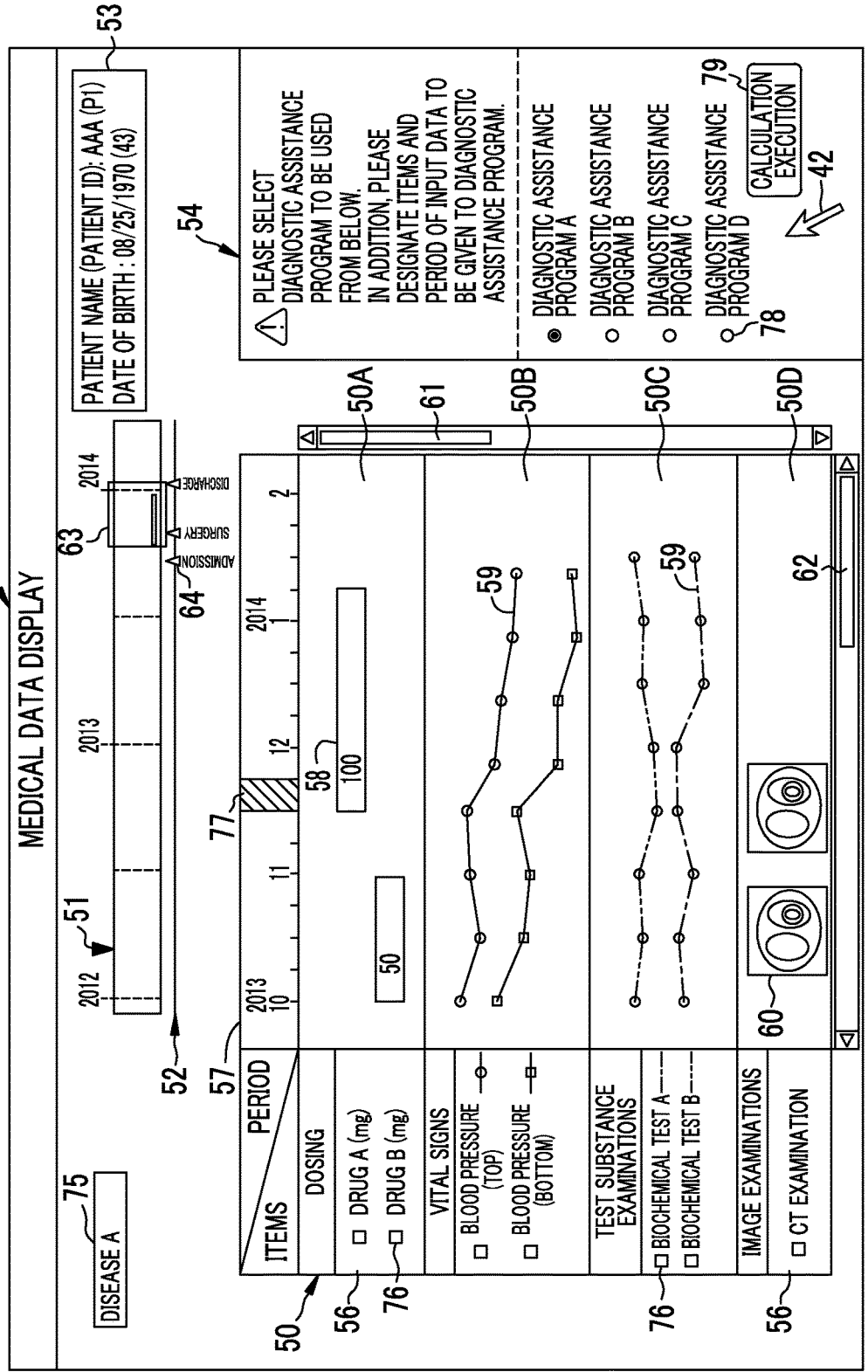
FIG. 7 is a diagram showing a medical data display screen for receiving the designation of a range and the selection of a diagnostic assistance program to be used.

In response to the display switching request including the disease ID, the display of the medical data display screen 15 is switched as shown in FIG. 7. FIG. 7 is an example when the "disease A" is selected in the pull-down menu 55. The display content of the medical data display screen 15 shown in FIG. 7 is basically the same as that of the medical data display screen 15 shown in FIG. 6, but is different in that the items of the medical data displayed in the medical data display region 50 have been changed. FIG. 7 shows a state in which the line graphs 59 regarding the "body temperature" and the "biochemical test C" displayed in FIG. 6 have been removed.

The switching of the items of the medical data is performed based on a disease-specific list 80 shown in FIG. 8. In FIG. 8, the disease-specific list 80 is a list obtained by recording the item (hereinafter, referred to as a display item) of medical data displayed on the medical data display screen 15 and the diagnostic assistance program 101 so as to be associated with each other for each type of disease, such as the disease A and the disease B. For example, for the "disease A", items of "drug A, drug B", "blood pressure (top), blood pressure (bottom)", "biochemical test A, biochemical test B", and "CT examination" are registered as display items, and a plurality of "diagnostic assistance programs (PR1), (PR2), . . . " are registered as the diagnostic assistance programs 101. In addition, for the "complex diseases AB" in which the "disease A" and the "disease B" are combined, items of "drug A, drug B, drug C", "blood pressure (top), blood pressure (bottom)", "biochemical test A, biochemical test B, biochemical test F, biochemical test G", "blood test E", "CT examination", and "ultrasonic examination" are registered as display items, and diagnostic assistance programs (PR100), . . . are registered as the diagnostic assistance programs 101.

Figure 15:
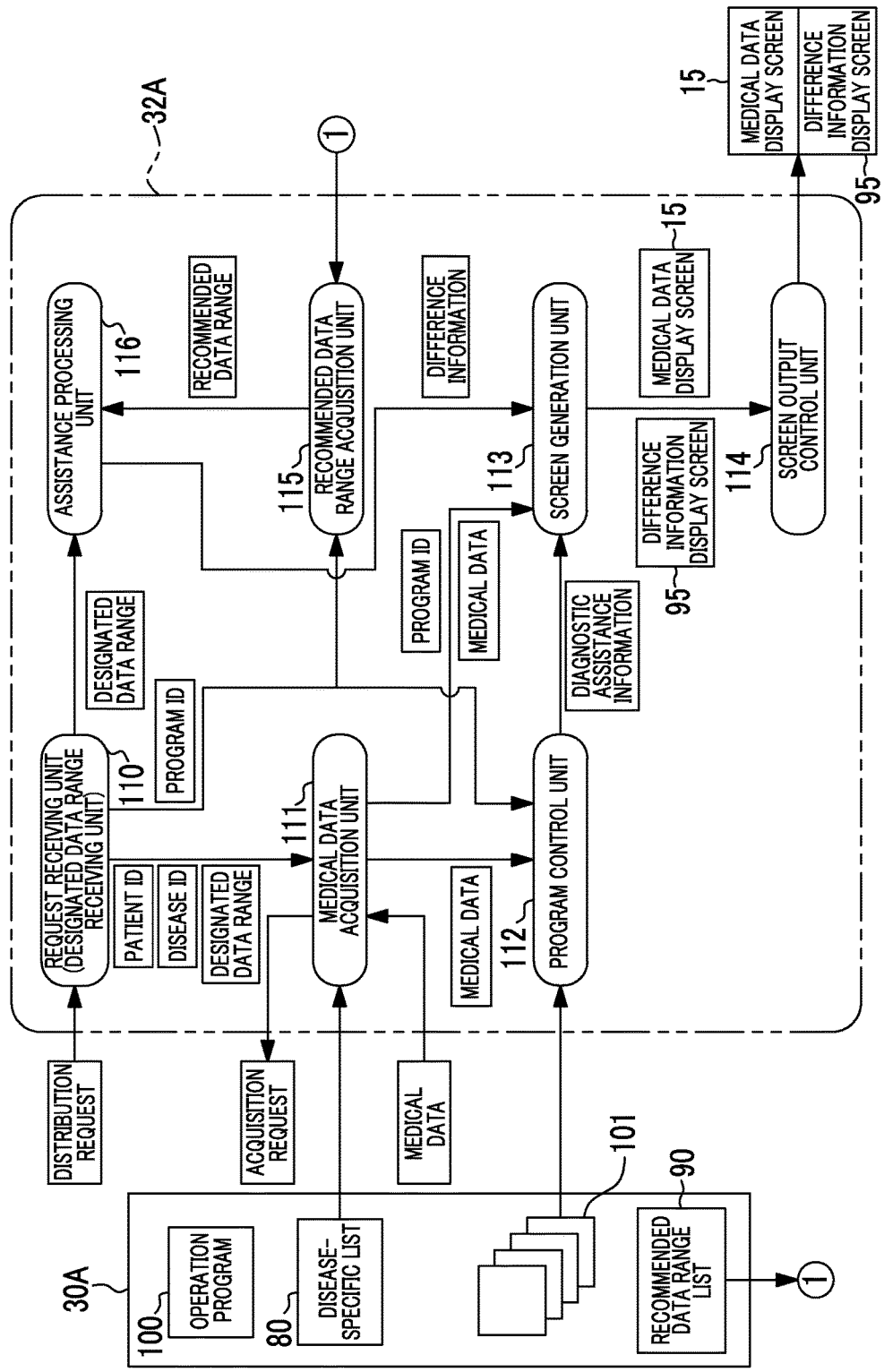
FIG. 15 is a block diagram showing functional units of a CPU of a medical assistance server and the flow of various kinds of information.

The disease-specific list 80 is stored in the storage device 30A of the medical assistance server 11 (refer to FIG. 15). The display items and the diagnostic assistance program 101 of the disease-specific list 80 are registered in advance by the administrator of the medical assistance server 11 or the doctor who operates the client terminal 12. The display items and the diagnostic assistance program 101 of the disease-specific list 80 can be updated when necessary. In addition, "D1", "D1+D2", and the like in the parentheses after the disease indicate disease IDs. In addition, "PR1", "PR20", "PR100", and the like in the parentheses after the diagnostic assistance program 101 indicate program IDs.

In FIG. 7, on the medical data display screen 15, a disease display region 75 is provided instead of the pull-down menu 55, the OK button 65, and the add button 66 in FIG. 6. In the disease display region 75, the name (in this example, "disease A") of the disease selected in the pull-down menu 55 is displayed.

In addition, a check box 76 for designating each item in the input data is displayed in the item display column 56, and a period designating bar 77 (indicated by hatching of oblique lines) for designating the period of the input data is displayed in the period display column 57. In addition, a message prompting the selection of the diagnostic assistance program 101 to be used and the designation of the item of the input data and the period is displayed in the various information display region 54. In the various information display region 54, the names of the diagnostic assistance programs 101 set in the disease-specific list 80 are listed, and a radio button 78 for selecting one diagnostic assistance program 101 among the displayed diagnostic assistance programs 101 and a calculation execution button 79 are displayed.

On the medical data display screen 15 in FIG. 9, as shown by a check mark in the check box 76, a state is shown in which "drug A, drug B", "blood pressure (top), blood pressure (bottom)", and "biochemical test A" are designated as designated data items, two weeks of the third and fourth weeks in November, 2013 are designated as a designated data period, and "diagnostic assistance program A" is selected as the diagnostic assistance program 101 to be used by the radio button 78. As shown in the medical data display screen 15 in FIG. 9, when the check box 76 of a desired item is designated by the cursor 42, the width of the period designating bar 77 is set to a desired period, the desired diagnostic assistance program 101 is selected by the radio button 78, and the calculation execution button 79 is clicked, a display switching request including a designated data range, which includes the item designated by the check box 76 as a designated data item and the period designated by the period designating bar 77 as a designated data period, and the program ID of the diagnostic assistance program 101 selected by the radio button 78 is transmitted from the client terminal 12 to the medical assistance server 11. As the period designated by the period designating bar 77, it is possible to mention not only a predetermined period from the start of dosing of certain drugs illustrated in FIG. 10 but also a predetermined period from the date on which an event of surgery or the like occurs and a period for which the user wants to see a change in the lesion of cancer or the like.

Instead of listing the name of the diagnostic assistance program 101 or in addition to listing the name of the diagnostic assistance program 101, the intended use of each diagnostic assistance program 101 may be displayed in the various information display region 54. The intended use indicates for which purpose the diagnostic assistance program 101 has been created. For example, "lesion measurement" is displayed as the intended use in the case of the diagnostic assistance program 101 for measuring the lesion size, and "side effects detection" is displayed as the intended use in the case of the diagnostic assistance program 101 for detecting the side effects of the drug.

Figure 10:
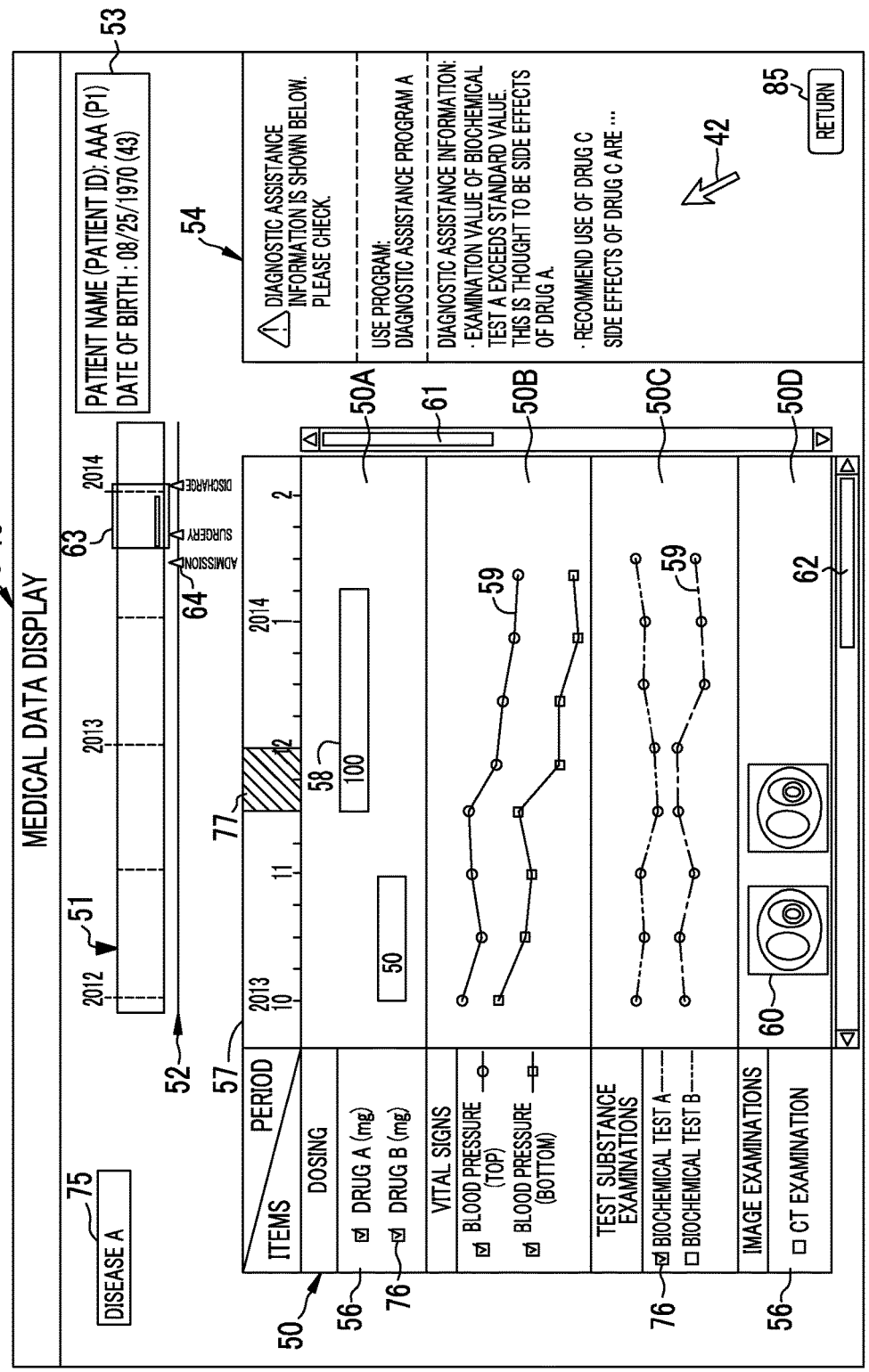
FIG. 10 is a diagram showing a medical data display screen on which diagnostic assistance information is displayed.

In response to the display switching request including the designated data range and the program ID, the display of the medical data display screen 15 is switched as shown in FIG. 10. The display content of the medical data display screen 15 shown in FIG. 10 is basically the same as that of the medical data display screen 15 shown in FIG. 9, but the content displayed in the various information display region 54 is different. Specifically, a message prompting the confirmation of diagnostic assistance information, the name of the used diagnostic assistance program 101, diagnostic assistance information, and a return button 85 for returning the display to the state shown in FIG. 9 are displayed in the various information display region 54. In FIG. 10, findings about the examination value of "biochemical test A", comments that recommend the use of "drug C" other than "drugs A and B", and comments regarding the side effects of "drug C" are illustrated as diagnostic assistance information.

In FIG. 11, in a recommended data range list 90, a recommended data range is recorded for each diagnostic assistance program 101. The recommended data range list 90 is stored in the storage device 30A of the medical assistance server 11 (refer to FIG. 15). That is, the storage device 30A corresponds to a storage unit.

The recommended data range is a range that is set by the development company of the diagnostic assistance program 101 in advance and is recommended for the range of medical data to be used for the input data of the diagnostic assistance program 101. The recommended data range includes a recommended data item and a recommended data period. The recommended data item is an item that corresponds to the designated data item and is recommended as an item to be used for the input data among the items of medical data. The recommended data period is a period that corresponds to the designated data period and is recommended as a period to be used for the input data among the pieces of medical data in the entire course of treatment for the patient. For example, for the "diagnostic assistance program (PR1)", items of "drug A", "blood pressure (top), blood pressure (bottom), pulse, body temperature", and "biochemical test A" are registered as the recommended data items, and "one month from the dosing date of drug A" is registered as the recommended data period. As the recommended data period, only a period, such as "one month or more", may be simply set without designating the specific date and time, such as the dosing date and time of the drug A in the example described above. In this case, for example, a minimum period required to execute the diagnostic assistance program 101 is set.

The recommended data range is a range of input data for outputting the reliable diagnostic assistance information by the execution of the diagnostic assistance program 101.

There are two cases in which there is a difference between the designated data range and the recommended data range. That is, these are a case in which there is surplus data that is medical data outside the recommended data range and inside the designated data range and a case in which there is missing data that is medical data outside the designated data range and inside the recommended data range.

Figure 12:
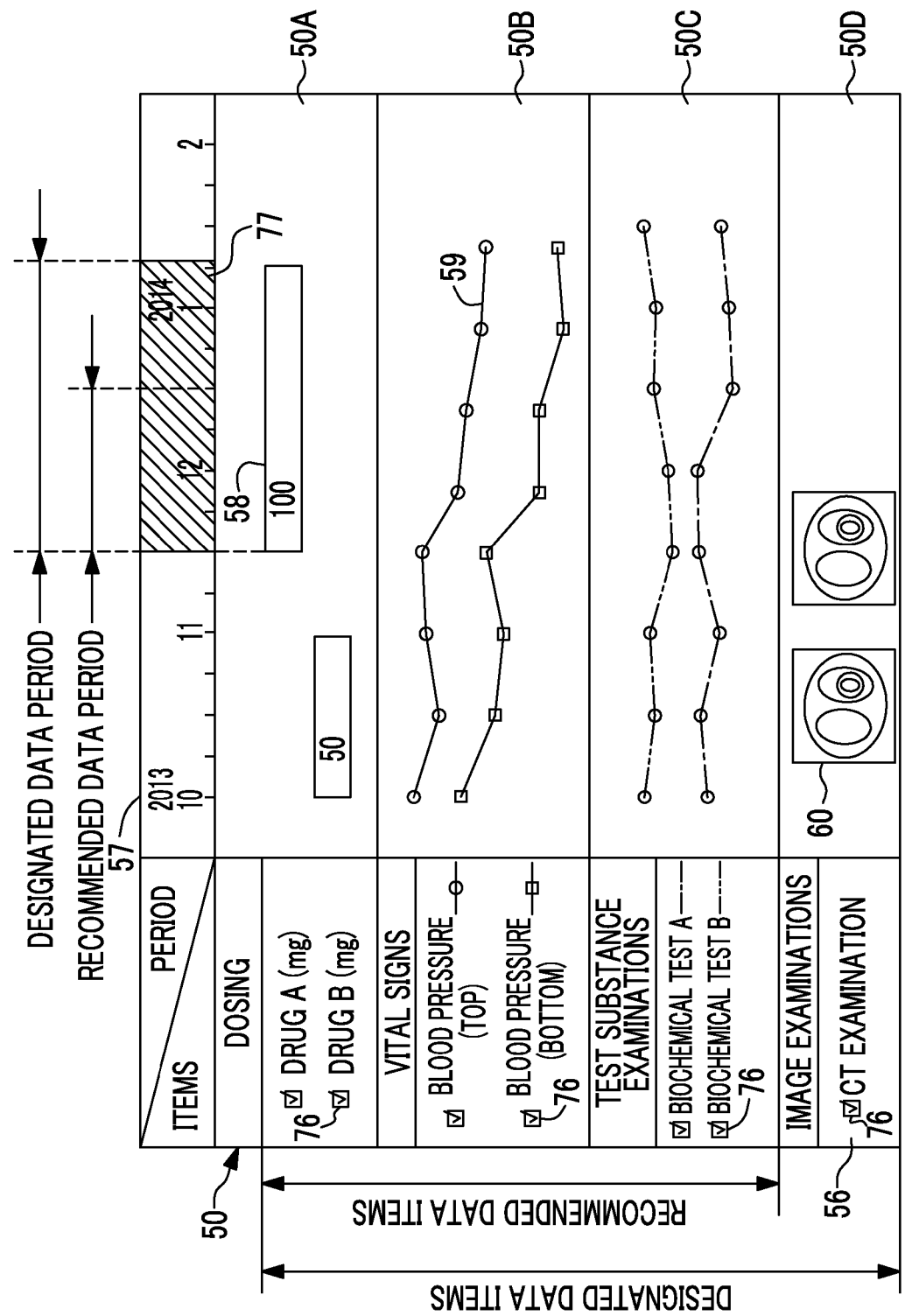
FIG. 12 is a diagram showing an example of range designation when there is surplus data which is data outside the recommended data range and inside a designated data range.

For example, as shown in FIG. 12, the case in which there is surplus data is a case in which the recommended data items are "drug A, drug B", "blood pressure (top), blood pressure (bottom)", and "biochemical test A, biochemical test B" and the designated data items are the recommended data items and "CT examination", that is, a case in which there is a surplus item other than the recommended data items in the designated data items. Alternatively, the case in which there is surplus data is a case in which the recommended data period is "one month from the dosing date of the drug A" and the designated data period is seven weeks from the dosing date of the drug A, that is, a case in which the designated data period extends off the recommended data period.

Figure 13:
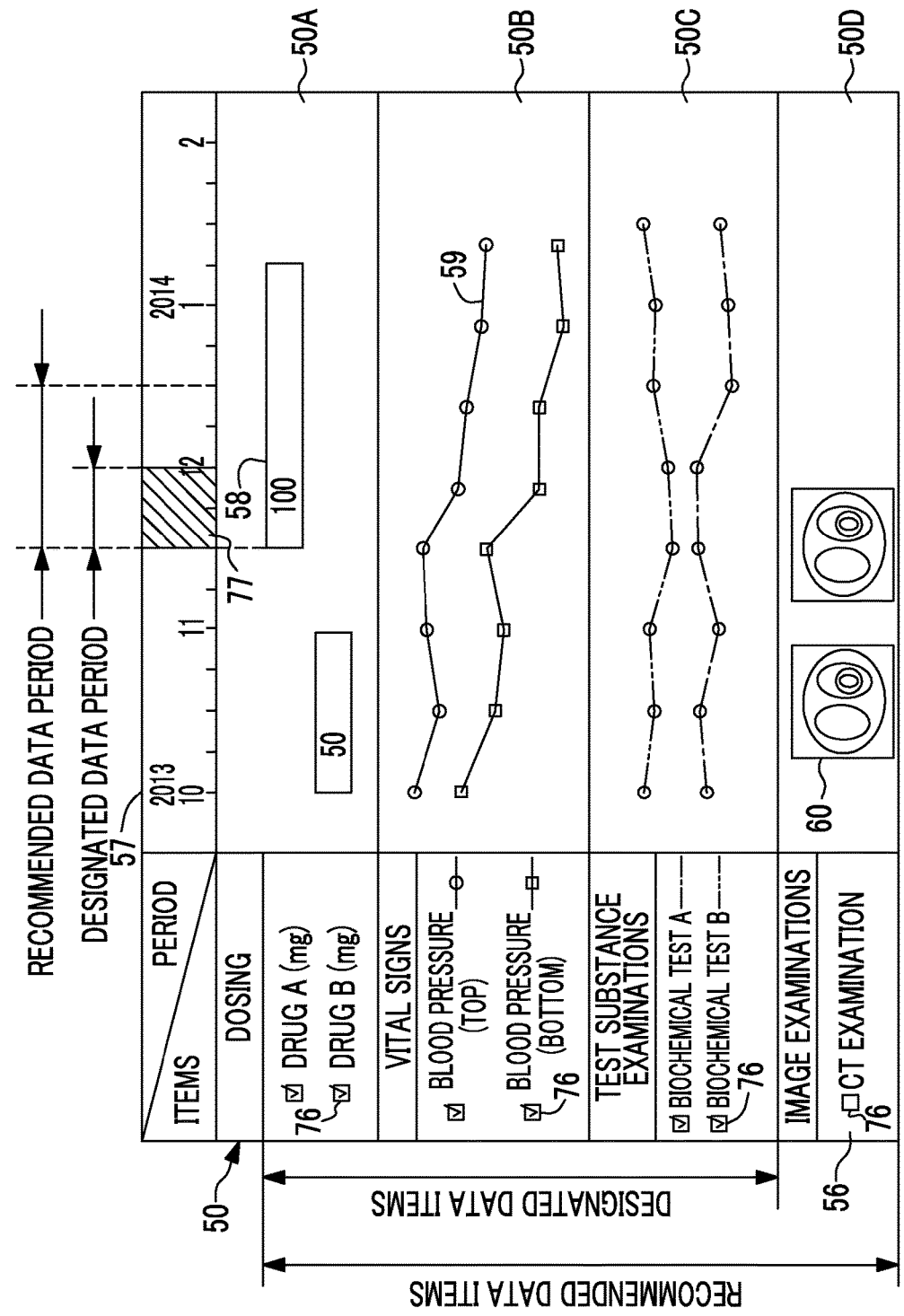
FIG. 13 is a diagram showing an example of range designation when there is missing data which is data outside the designated data range and inside a recommended data range.

On the other hand, for example, as shown in FIG. 13, the case in which there is missing data is a case in which the recommended data items are "drug A, drug B", "blood pressure (top), blood pressure (bottom)", "biochemical test A, biochemical test B", and "CT examination" and the designated data items are the recommended data items excluding "CT examination", that is, a case in which the number of designated data items is smaller than the number of recommended data items or a case in which the recommended data period is "one month from the dosing date of the drug A" and the designated data period is two weeks from the dosing date of the drug A, that is, a case in which the designated data period is shorter than the recommended data period.

Figure 14:
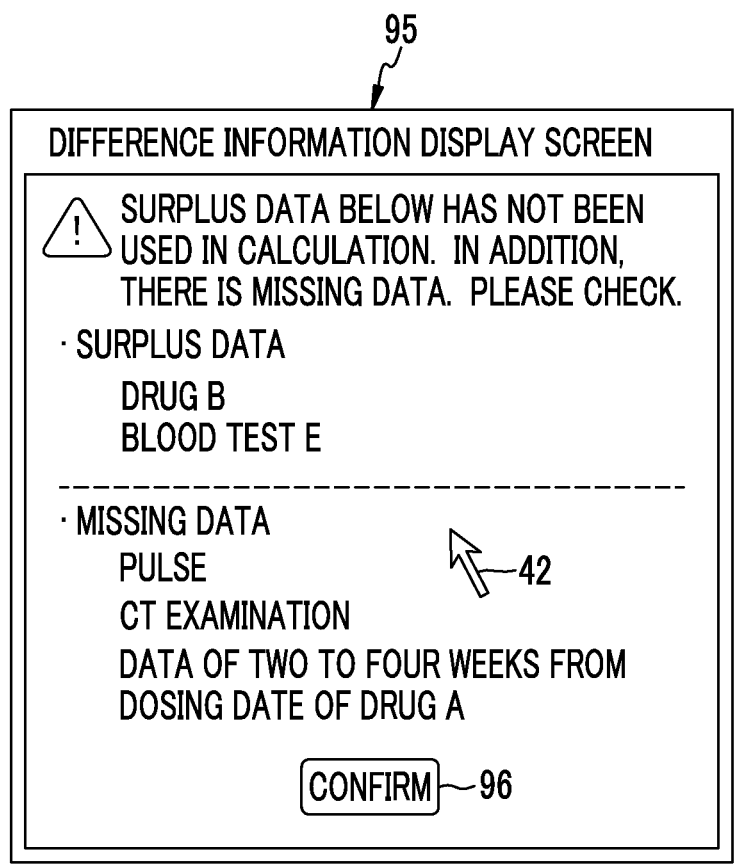
FIG. 14 is a diagram showing a difference information display screen.

Thus, in a case where there is a difference between the designated data range and the recommended data range, a difference information display screen 95 shown in FIG. 14 pops up on the medical data display screen 15 shown in FIG. 10.

In FIG. 14, a message showing that there is surplus data and the surplus data has not been used for the execution of the diagnostic assistance program 101, a message showing that there is missing data, specific content of the surplus data and the missing data, and a confirm button 96 for removing the display of the difference information display screen 95 are displayed on the difference information display screen 95. In FIG. 14, medical data of the items of "drug B" and "blood test E" are illustrated as information regarding surplus data, and medical data of the items of "pulse", "CT examination", and "two to four weeks from the dosing date of drug A" are illustrated as information regarding missing data.

Although FIG. 14 is a case in which both the surplus data and the missing data are picked up, there is also a case in which one of the surplus data and the missing data is picked up. In this case, information regarding only one of the surplus data and the missing data that is picked up is displayed on the difference information display screen 95. In addition, medical data used for the execution of the diagnostic assistance program 101 may also be displayed on the difference information display screen 95 together with the information regarding the surplus data and the information regarding the missing data.

The case in which there is surplus data is, for example, a case in which a doctor designates a range considered to affect the diagnosis but the designated range is not in the recommended data range and the diagnostic assistance program 101 does not correspond thereto. In such a case, if the difference information display screen 95 shows that there is surplus data, the doctor can see that the range designated by himself or herself is not reflected on the diagnostic assistance information, and can determine not to adopt the diagnostic assistance information at the time of diagnosis. In addition, when the surplus data is displayed on the difference information display screen 95, the doctor himself or herself can check the specific content of the surplus data. When it is determined that the surplus data does not affect the diagnosis as the doctor thought as a result of the checking, the doctor may also determine to adopt the diagnostic assistance information. If it is not known which kind of medical data was used for executing the diagnostic assistance program 101, it becomes difficult for the doctor to use the diagnostic assistance program 101. However, by specifying that there is surplus data in this manner, the doctor can use the diagnostic assistance program 101 with confidence.

On the other hand, the case in which there is missing data is a case in which a doctor does not designate the medical data of the recommended data range by mistake when designating a range. In such a case, if the difference information display screen 95 shows that there is missing data, it is possible to prevent the doctor from performing diagnosis while mistakenly believing that the diagnostic assistance information is reliable.

In FIG. 15, an operation program 100 and a plurality of diagnostic assistance programs 101 are stored in the storage device 30A of the medical assistance server 11 as application programs. The operation program 100 is a program for operating a computer, which forms the medical assistance server 11, as a medical assistance device.

In addition to the various programs, the disease-specific list 80 shown in FIG. 8 and the recommended data range list 90 shown in FIG. 11 are stored in the storage device 30A.

When the operation program 100 starts, the CPU 32A of the medical assistance server 11 cooperates with the memory 31 to function as the request receiving unit 110, a medical data acquisition unit 111, a program control unit 112, a screen generation unit 113, a screen output control unit 114, a recommended data range acquisition unit 115, and an assistance processing unit 116.

The request receiving unit 110 has a request receiving function of receiving a distribution request and a display switching request transmitted from the client terminal 12. More specifically, the request receiving unit 110 receives a distribution request including a patient ID. In addition, the request receiving unit 110 receives a display switching request including a disease ID, a program ID, and a designated data range. That is, the request receiving unit 110 corresponds to a designated data range receiving unit. The request receiving unit 110 transmits a patient ID and a disease ID to the medical data acquisition unit 111, transmits a program ID to the program control unit 112 and the recommended data range acquisition unit 115, and transmits a designated data range to the medical data acquisition unit 111 and the assistance processing unit 116.

The medical data acquisition unit 111 has a medical data acquisition function of acquiring desired medical data.

When a patient ID from the request receiving unit 110 is received, the medical data acquisition unit 111 outputs an acquisition request having the patient ID as a search keyword to the communication unit 33A (not shown). In response to the acquisition request, medical data in the entire course of treatment for the patient, which is transmitted from the server group 13 and is received by the communication unit 33A, is acquired. The medical data acquisition unit 111 stores the acquired medical data in the storage device 30A, and transmits the acquired medical data to the screen generation unit 113.

When a disease ID from the request receiving unit 110 is received, the medical data acquisition unit 111 reads the program ID of the diagnostic assistance program 101 and a display item corresponding to the received disease ID from the disease-specific list 80. The medical data acquisition unit 111 extracts medical data corresponding to the display item read from the disease-specific list 80 from the medical data in the entire course of treatment for the patient, which is acquired in response to the acquisition request and is stored in the storage device 30A, and transmits the extracted medical data and the program ID read from the disease-specific list 80 to the screen generation unit 113.

When the designated data range from the request receiving unit 110 is received, the medical data acquisition unit 111 extracts medical data corresponding to the received designated data range from the medical data in the entire course of treatment for the patient, which is acquired in response to the acquisition request and is stored in the storage device 30A, and transmits the extracted medical data to the program control unit 112.

The program control unit 112 has a program control function of controlling the diagnostic assistance program 101. In other words, the diagnostic assistance program 101 is executed under the control of the program control unit 112.

When a program ID from the request receiving unit 110 is received, the program control unit 112 reads the diagnostic assistance program 101 corresponding to the received program ID from the plurality of diagnostic assistance programs 101 stored in the storage device 30A. The program control unit 112 executes the diagnostic assistance program 101 by giving the medical data of the designated data range received from the medical data acquisition unit 111, as input data, to the read diagnostic assistance program 101, and outputs diagnostic assistance information. The program control unit 112 transmits the diagnostic assistance information to the screen generation unit 113.

The diagnostic assistance information is information for assisting the diagnosis of a patient by a doctor. In addition to the image analysis information such as the size or type of a lesion in the examination image 24, findings about the examination value, and the presence or absence of side effects from dosing that have been described above, measurement values, a decrease in the examination value, an increase rate, and the like can be mentioned as examples of the diagnostic assistance information. In addition, the diagnostic assistance information may be any information useful for diagnosis, such as the presentation of recommended drugs based on genetic test information.

The screen generation unit 113 has a screen generation function of generating various operation screens, such as the medical data display screen 15. The screen generation unit 113 generates the medical data display screen 15 based on the medical data. In addition, the screen generation unit 113 switches the display of the medical data display screen 15 from FIG. 6 to FIG. 7 or 10 in response to the display switching request. In addition, the screen generation unit 113 generates the difference information display screen 95. Through the difference information display screen 95, difference information is presented to the doctor. The screen generation unit 113 transmits the generated various operation screens, such as the medical data display screen 15, to the screen output control unit 114.

The screen output control unit 114 has a screen output control function of outputting the various operation screens received from the screen generation unit 113 to the communication unit 33A. The screen output control unit 114 outputs the medical data display screen 15 and information of the client terminal 12, which has sent the distribution request or the display switching request (for example, Internet protocol (IP) address of the client terminal 12), to the communication unit 33A.

The recommended data range acquisition unit 115 has a recommended data range acquisition function of acquiring a recommended data range. The recommended data range acquisition unit 115 reads a recommended data range corresponding to the program ID, which is received from the request receiving unit 110, from the recommended data range list 90. The recommended data range acquisition unit 115 transmits the read recommended data range to the assistance processing unit 116.

The assistance processing unit 116 has an assistance processing function of outputting assistance information for assisting the diagnosis of a doctor using the diagnostic assistance program 101 in order to present it to the doctor. The assistance processing unit 116 outputs, as the assistance information, difference information indicating that there is a difference between the designated data range and the recommended data range.

Figure 16:
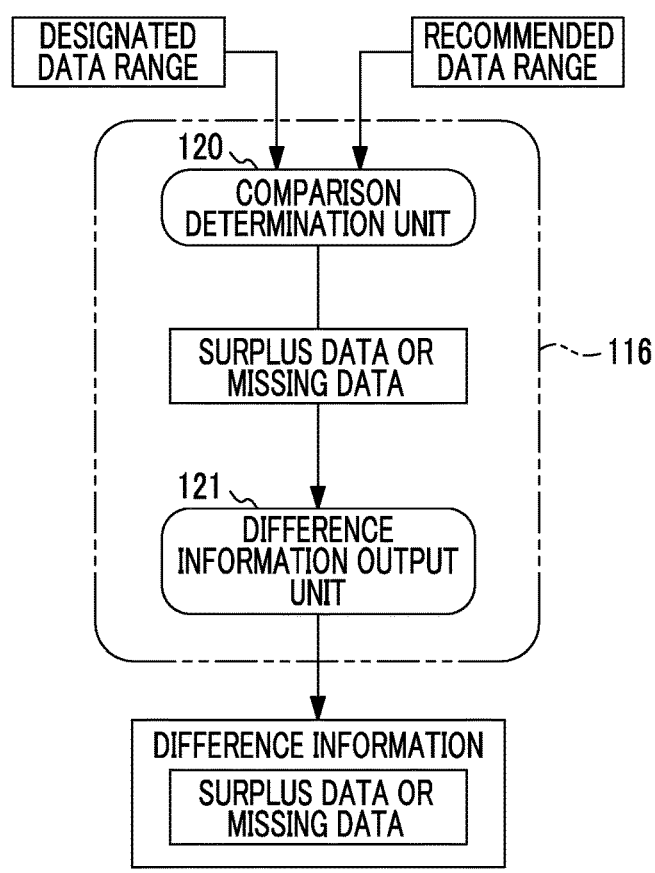
FIG. 16 is a block diagram showing the detailed configuration of an assistance processing unit.

Specifically, as shown in FIG. 16, the assistance processing unit 116 includes a comparison determination unit 120 and a difference information output unit 121. The comparison determination unit 120 compares the designated data range received from the request receiving unit 110 with the recommended data range received from the recommended data range acquisition unit 115. The comparison determination unit 120 determines whether or not there is a difference between the designated data range and the recommended data range.

When there is a difference between the designated data range and the recommended data range, the comparison determination unit 120 picks up information regarding the surplus data, which is medical data outside the recommended data range, from the medical data designated by the designated data range. Alternatively, the comparison determination unit 120 picks up information regarding the missing data that is medical data deficient in the designated data range with respect to the medical data designated in the recommended data range. The comparison determination unit 120 outputs the information regarding the surplus data and the information regarding the missing data, which have been picked up, to the difference information output unit 121. The difference information output unit 121 outputs the information regarding the surplus data and the information regarding the missing data from the comparison determination unit 120, as difference information, to the screen generation unit 113.

Referring to the examples shown in FIGS. 12 and 13, in the example shown in FIG. 12, the comparison determination unit 120 picks up the medical data of "CT examination", which is a designated data item but is not a recommended data item, and the item of "five to seven weeks from the dosing date of drug A", which is in the designated data period but is outside the recommended data period, as the information regarding surplus data. In the example shown in FIG. 13, the comparison determination unit 120 picks up the medical data of "CT examination", which is a recommended data item but is not a designated data item, and the item of "three to four weeks from the dosing date of drug A", which is in the recommended data period but is outside the designated data period, as the information regarding missing data.

When the designated data range matches the recommended data range, it is natural that the information regarding surplus data and the information regarding missing data are not output from the comparison determination unit 120 and the difference information is not output from the difference information output unit 121 either.

When there is surplus data, the program control unit 112 executes the diagnostic assistance program 101 using only the medical data of the recommended data range as input data without using the surplus data as input data. When there is missing data, the program control unit 112 executes the diagnostic assistance program 101 using only the medical data of the designated data range as input data.

Figure 17:
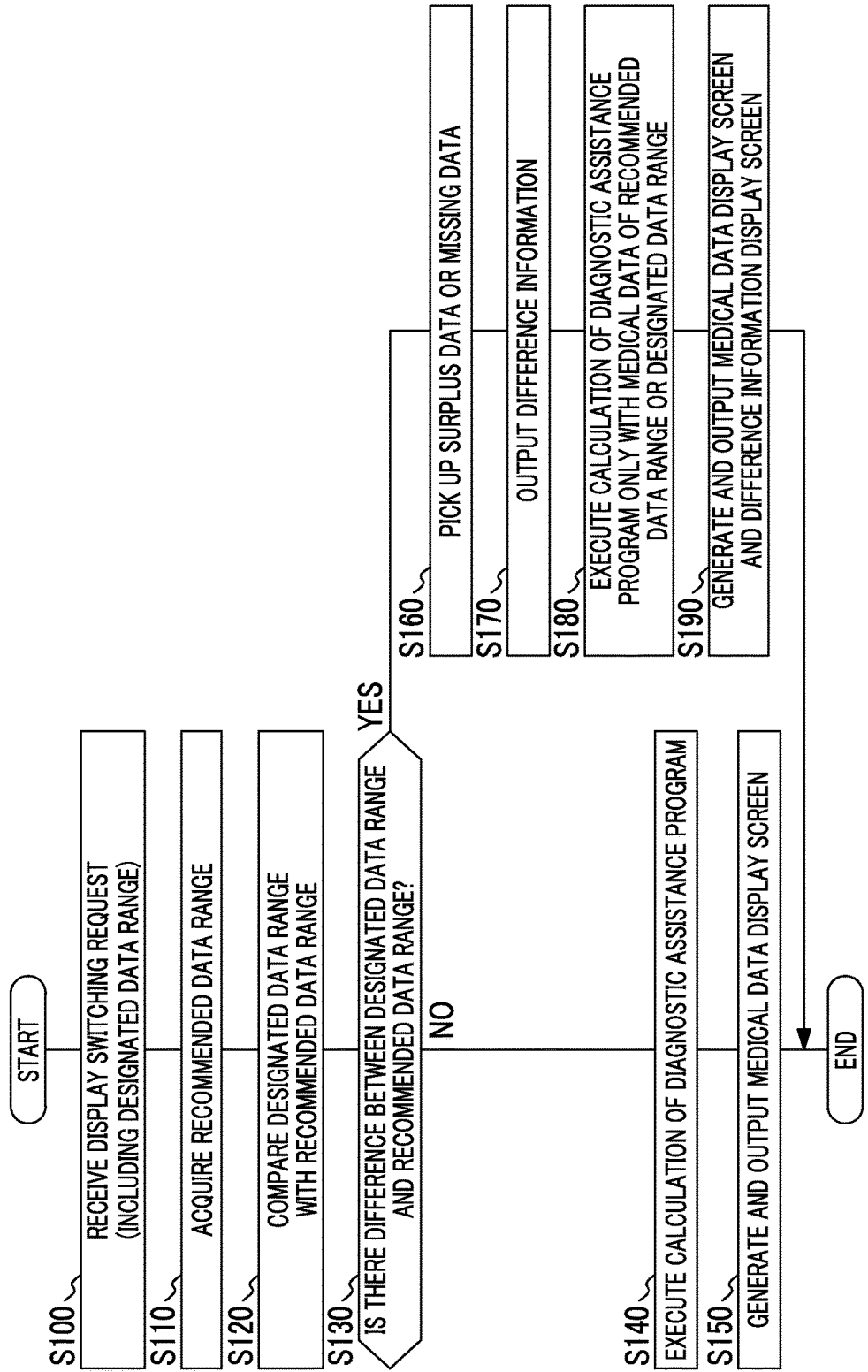
FIG. 17 is a flowchart showing the operation procedure of the functional units of the CPU of the medical assistance server.

Hereinafter, the operation of the above configuration will be described with reference to FIG. 17. First, the operation program 100 is started in the medical assistance server 11. Then, the request receiving unit 110, the medical data acquisition unit 111, the program control unit 112, the screen generation unit 113, the screen output control unit 114, the recommended data range acquisition unit 115, and the assistance processing unit 116 are built in the CPU 32A, and the computer that forms the medical assistance server 11 functions as a medical assistance device.

The doctor accesses the medical assistance server 11 on the web browser of the client terminal 12, and performs authorization for receiving the provision of medical assistance services by the medical assistance server 11. When authorization is performed, a startup screen for inputting a patient ID is displayed on the display 34B of the client terminal 12. The doctor inputs a patient ID of a patient whose medical data needs to be viewed on the startup screen. The patient ID input to the startup screen is transmitted from the client terminal 12 to the medical assistance server 11 as a distribution request.

In the medical assistance server 11, the distribution request from the client terminal 12 is received by the communication unit 33A. The distribution request is output to the request receiving unit 110 from the communication unit 33A, and is received by the request receiving unit 110. The patient ID of the distribution request is transmitted from the request receiving unit 110 to the medical data acquisition unit 111.

From the medical data acquisition unit 111, an acquisition request having the patient ID of the distribution request as a search keyword is output to the communication unit 33A. As a result, the acquisition request is transmitted from the communication unit 33A to the server group 13.

In response to the acquisition request from the medical assistance server 11, the server group 13 searches for the medical data in the entire course of treatment for the patient corresponding to the acquisition request. Then, the searched medical data is transmitted to the medical assistance server 11.

The medical data in the entire course of treatment for the patient from the server group 13 is received by the communication unit 33A, and is output to the medical data acquisition unit 111 from the communication unit 33A. Thus, the medical data in the entire course of treatment for the patient is acquired. The medical data is stored in the storage device 30A by the medical data acquisition unit 111, and is transmitted to the screen generation unit 113.

In the screen generation unit 113, the medical data display screen 15 shown in FIG. 6 is generated based on the medical data in the entire course of treatment for the patient from the medical data acquisition unit 111. Then, the medical data display screen 15 is output to the communication unit 33A by the screen output control unit 114. As a result, the medical data display screen 15 is transmitted from the communication unit 33A to the client terminal 12. In the client terminal 12, the medical data display screen 15 shown in FIG. 6 is displayed on the display 34B.

The doctor selects the disease of the patient in the pull-down menu 55 of the medical data display screen 15, and clicks the OK button 65. Then, a display switching request including the disease ID of the disease selected in the pull-down menu 55 is transmitted from the client terminal 12 to the medical assistance server 11.

In the medical assistance server 11, the display switching request from the client terminal 12 is received by the communication unit 33A. The display switching request is output to the request receiving unit 110 from the communication unit 33A, and is received by the request receiving unit 110. The disease ID of the display switching request is transmitted from the request receiving unit 110 to the medical data acquisition unit 111.

The medical data acquisition unit 111 reads, from the disease-specific list 80, the program ID of the diagnostic assistance program 101 and a display item corresponding to the disease ID of the display switching request. Then, medical data corresponding to the display item read from the disease-specific list 80 is extracted from the medical data in the entire course of treatment for the patient stored in the storage device 30A. Then, the extracted medical data and the program ID read from the disease-specific list 80 are transmitted to the screen generation unit 113.

In the screen generation unit 113, the medical data display screen 15 shown in FIG. 7 is generated based on the program ID and the medical data corresponding to the display item read from the disease-specific list 80 by the medical data acquisition unit 111. Then, the medical data display screen 15 is output to the communication unit 33A by the screen output control unit 114. As a result, the medical data display screen 15 is transmitted from the communication unit 33A to the client terminal 12. In the client terminal 12, the medical data display screen 15 shown in FIG. 7 is displayed on the display 34B.

As illustrated in FIG. 9, the doctor designates a desired item using the check box 76 of the medical data display screen 15, and designates a desired period using the period designating bar 77. In addition, the doctor selects the desired diagnostic assistance program 101 using the radio button 78, and clicks the calculation execution button 79. As a result, a display switching request including the designated data range, in which the item designated by using the check box 76 is a designated data item and the period designated by using the period designating bar 77 is a designated data period, and the program ID of the diagnostic assistance program 101 selected by the radio button 78 is transmitted from the client terminal 12 to the medical assistance server 11.

In the medical assistance server 11, the display switching request including the program ID and the designated data range from the client terminal 12 is received by the communication unit 33A. As shown in step S100 of FIG. 17, the display switching request is output to the request receiving unit 110 from the communication unit 33A, and is received by the request receiving unit 110. The program ID of the display switching request is transmitted from the request receiving unit 110 to the program control unit 112 and the recommended data range acquisition unit 115, and the designated data range is transmitted from the request receiving unit 110 to the medical data acquisition unit 111 and the assistance processing unit 116.

The recommended data range acquisition unit 115 reads a recommended data range corresponding to the program ID, which is received from the request receiving unit 110, from the recommended data range list 90 (step S110). The recommended data range is transmitted from the recommended data range acquisition unit 115 to the assistance processing unit 116.

Then, assistance processing is performed by the assistance processing unit 116. Specifically, the comparison determination unit 120 compares the designated data range received from the request receiving unit 110 with the recommended data range received from the recommended data range acquisition unit 115 (step S120). Then, it is determined whether or not there is a difference between the designated data range and the recommended data range (step S130).

When the designated data range and the recommended data range match each other (NO in step S130), the assistance processing is ended. The medical data acquisition unit 111 extracts medical data corresponding to the designated data range of the display switching request from the medical data in the entire course of treatment for the patient, which is stored in the storage device 30A, and transmits the extracted medical data to the program control unit 112. Then, the program control unit 112 gives the medical data of the designated data range transmitted from the medical data acquisition unit 111, as input data, to the diagnostic assistance program 101 corresponding to the program ID transmitted from the request receiving unit 110, so that the calculation is performed (step S140). The diagnostic assistance information is output by executing the diagnostic assistance program 101 and performing calculation. The diagnostic assistance information is transmitted from the program control unit 112 to the screen generation unit 113.

In the screen generation unit 113, the medical data display screen 15 shown in FIG. 10 is generated based on the diagnostic assistance information. Then, the medical data display screen 15 is output to the communication unit 33A by the screen output control unit 114 (step S150). As a result, the medical data display screen 15 is transmitted from the communication unit 33A to the client terminal 12. In the client terminal 12, the medical data display screen 15 shown in FIG. 10 is displayed on the display 34B. The doctor performs diagnosis based on the diagnostic assistance information of the medical data display screen 15.

On the other hand, when there is a difference between the designated data range and the recommended data range (YES in step S130), information regarding the surplus data, which is data that is in the designated data range but is outside the recommended data range, or information regarding the missing data, which is data that is in the recommended data range but is outside the designated data range, is picked up by the comparison determination unit 120 (step S160). The information regarding the surplus data or the information regarding the missing data is output as difference information from the difference information output unit 121 to the screen generation unit 113 (step S170).

The program control unit 112 performs calculation based on the diagnostic assistance program 101 as in step S140. When there is surplus data, the calculation is performed only with the medical data of the recommended data range without using the surplus data. When there is missing data, the calculation is performed only with the medical data of the designated data range (step S180).

According to the medical assistance system 10 of the present embodiment, the diagnostic assistance program 101 is executed even if there is surplus data or missing data. Therefore, even if there is surplus data or missing data, it is possible to provide the diagnostic assistance information for the viewing of the doctor. The doctor may determine whether or not the diagnostic assistance information is reliable based on the difference information. By performing the calculation in this manner, when there is surplus data or missing data, it is possible to improve the diagnostic efficiency, compared with a case in which error processing is performed without executing the diagnostic assistance program 101 and outputting the diagnostic assistance information. In particular, when there is surplus data and there is no missing data, diagnostic assistance information that is not changed at all from that in the case in which the designated data range matches the recommended data range is output. Therefore, the effect of outputting the diagnostic assistance information is large.

Also in this case, as in the case of NO in step S130, the diagnostic assistance information is transmitted from the program control unit 112 to the screen generation unit 113. In the screen generation unit 113, the medical data display screen 15 shown in FIG. 10 and the difference information display screen 95 are generated based on the diagnostic assistance information. Then, the medical data display screen 15 and the difference information display screen 95 are output to the communication unit 33A by the screen output control unit 114 (step S190). As a result, the medical data display screen 15 and the difference information display screen 95 are transmitted from the communication unit 33A to the client terminal 12. In the client terminal 12, the medical data display screen 15 shown in FIG. 10 is displayed on the display 34B. In addition, the difference information display screen 95 is pop-up displayed on the medical data display screen 15.

When there is surplus data, it is necessary to notify the doctor that diagnostic assistance information based on the calculation performed without using the surplus data as input data has been output. If there is no such information, the doctor may perform diagnosis by mistakenly believing that all the items or the period designated by the doctor himself or herself has been used for the output of diagnostic assistance information. In addition, diagnostic assistance information that is output when there is missing data is output in a state in which data is deficient compared with the recommended data range. That is, even though there is input data that should be included in the calculation, diagnostic assistance information may be output by force. For this reason, the reliability of the diagnostic assistance information is not guaranteed. Also in this case, if the doctor is not notified of such a situation, the doctor may perform diagnosis while mistakenly believing that the diagnostic assistance information is reliable.

However, in the present embodiment, the doctor is notified that there is a difference between the designated data range and the recommended data range by displaying the difference information display screen 95. Therefore, since the doctor can see that the diagnostic assistance information displayed on the medical data display screen 15 has been output without using the surplus data as input data or that there is missing data and the reliability of the diagnostic assistance information is low, it is possible to make a diagnosis with this in mind. Therefore, it is possible to prevent the doctor from performing diagnosis by mistakenly believing that the item or the period designated by the doctor himself or herself has been used for the output of diagnostic assistance information or from performing diagnosis by mistakenly believing that the diagnostic assistance information is reliable. As a result, it is possible to use the diagnostic assistance program 101 with confidence.

In recent years, the selection of drugs for each patient according to the genetic test information of each patient has been considered. However, all patients do not necessarily undergo genetic testing. Therefore, when the diagnostic assistance program 101 has been developed according to the algorithm using genetic test information and the genetic test information has been registered as the recommended data item, a case occurs in which there is no genetic test information depending on a patient and this becomes missing data. When presenting the recommended drugs based on genetic test information as diagnostic assistance information, if it is specified that the genetic test information is missing data, it is possible to notify the doctor of whether or not the recommended drugs are based on the genetic test information of the patient. In this case, it is possible to take measures, such as starting the diagnostic assistance program 101 again after performing genetic testing additionally and then selecting drugs corresponding to the genetic test information. Accordingly, this is user-friendly for the doctor.

In addition, when information regarding the missing data is displayed on the difference information display screen 95, the doctor can return to the medical data display screen 15 shown in FIG. 9 to designate deficient medical data, so that it is possible to execute the diagnostic assistance program 101 again and to re-acquire the reliable diagnostic assistance information.

The medical data display screen 15 is a screen in which the examination image 24 and various kinds of data included in the electronic medical record 23 are collectively displayed as medical data within one screen. Therefore, it is possible to smoothly proceed with the diagnosis, compared with a case in which the electronic medical record 23 and the examination image 24 are viewed in separate display screens.

In addition, the medical data display screen 15 is a screen that is common to a plurality of diagnostic assistance programs 101 used in the medical assistance server 11. Therefore, usability is good rather than preparing a plurality of medical data display screens corresponding to the respective diagnostic assistance programs 101.

In the medical data display screen 15, medical data is displayed in the medical data display region 50 near the center of the screen, and diagnostic assistance information is displayed in the various information display region 54 located on the periphery of the screen. In the various information display region 54, a button prompting the confirmation of the diagnostic assistance information or a button for removing the display is not displayed. Therefore, the doctor can freely refer to the diagnostic assistance information without stress of the button selection operation.

When the number of diagnostic assistance programs 101 is small, it may be considered to perform control to generate a screen for designating a range for each diagnostic assistance program 101 and display the recommended data range so that the recommended data range is reliably designated on the screen for designating a range. In this case, since it cannot happen that the designated data range differs from the recommended data range, it is not necessary to output the difference information. However, it is expected that many kinds of diagnostic assistance programs 101 will be developed and be obsolete quickly in the future. For this reason, it is difficult to prepare a screen for designating a range for each diagnostic assistance program 101 and perform control so that the recommended data range is reliably designated on the screen for designating each range. Therefore, the method of outputting the difference information to present it to a doctor as in the present embodiment can be said to be a method considering the future development of the diagnostic assistance program 101.

Figure 18:
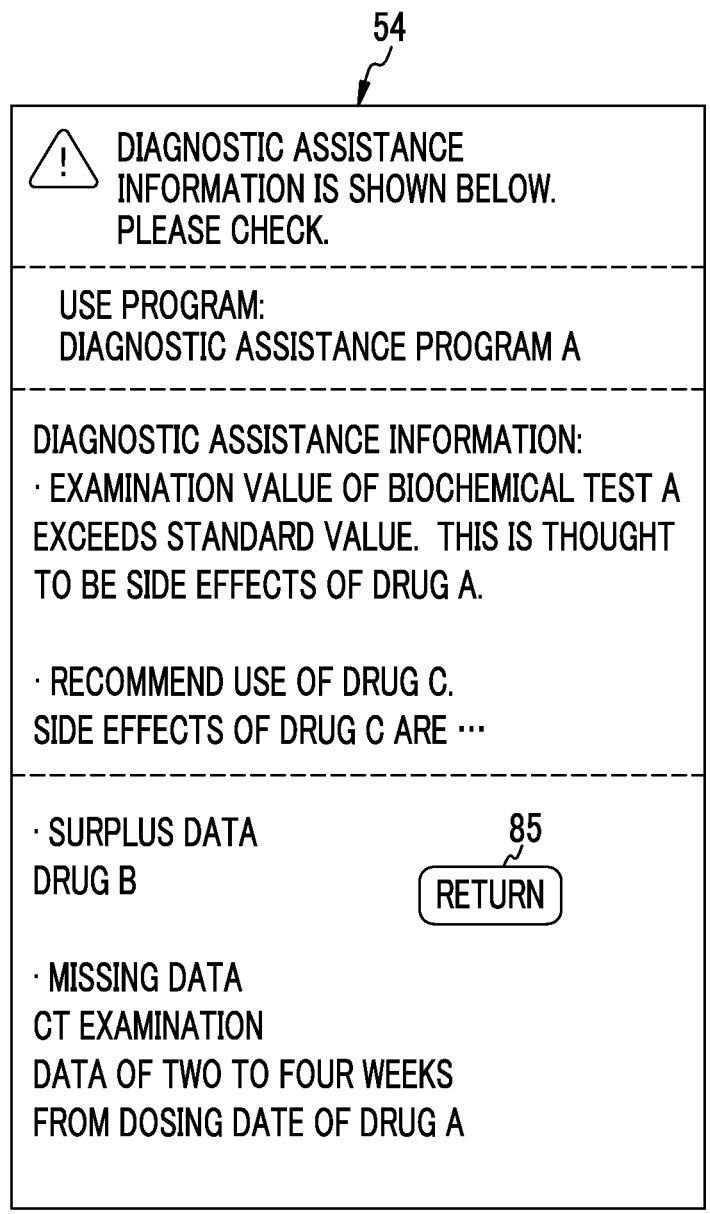
FIG. 18 is a diagram showing a medical data display screen on which diagnostic assistance information and difference information are displayed.

In the first embodiment described above, when there is a difference between the designated data range and the recommended data range, the difference information display screen 95 is pop-up displayed on the medical data display screen 15, so that the diagnostic assistance information and the difference information are displayed on different screens. However, as shown in FIG. 18, not only the diagnostic assistance information but also the difference information may be displayed in the various information display region 54 of the medical data display screen 15. Alternatively, as shown in FIG. 19, the screen generation unit 113 may generate a diagnostic assistance information and difference information display screen 125, on which both the diagnostic assistance information and the difference information are displayed, separately from the medical data display screen 15, and the diagnostic assistance information and difference information display screen 125 may be transmitted to the client terminal 12 and be displayed in the client terminal 12. Since both the diagnostic assistance information and the difference information are displayed on the diagnostic assistance information and difference information display screen 125, the doctor can see more clearly whether or not the diagnostic assistance information is reliable. In addition, a confirm button 126 shown in FIG. 19 is a button for removing the display of the diagnostic assistance information and difference information display screen 125.

Second Embodiment

In the first embodiment described above, when there is missing data, the diagnostic assistance program 101 is executed based on only the medical data of the designated data range. However, when significantly unreliable diagnostic assistance information is output, the diagnostic assistance information cannot be used for diagnosis. In this case, it is meaningless to execute the diagnostic assistance program 101. Therefore, in the present embodiment, even if there is missing data, diagnostic assistance information that is reliable to some extent is output to the diagnostic assistance program 101 by supplementing the missing data with appropriate supplementary data.

Figure 20:
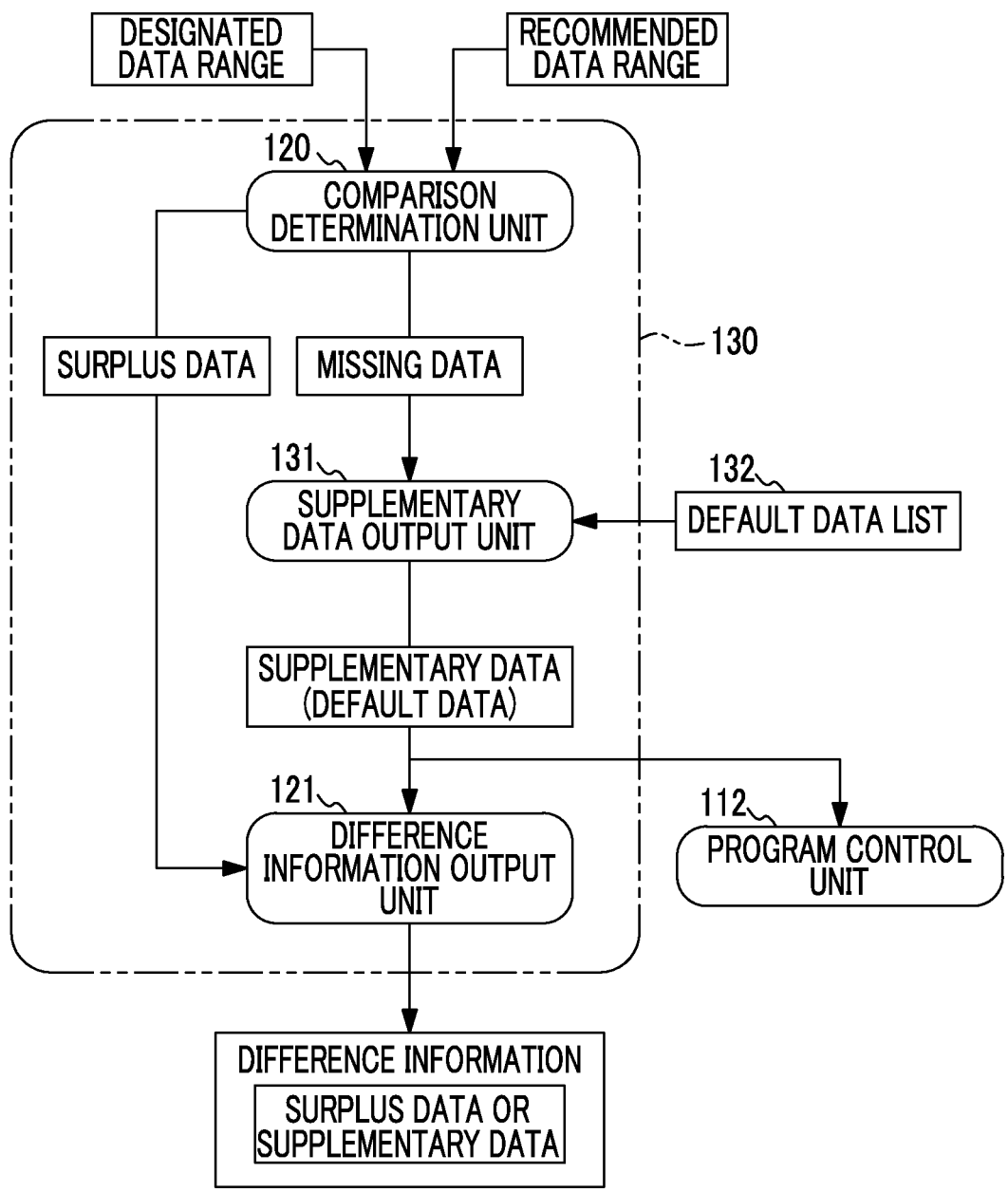
FIG. 20 is a block diagram showing the detailed configuration of an assistance processing unit including a supplementary data output unit in a second embodiment.

In FIG. 20, an assistance processing unit 130 built in the CPU of the medical assistance server of the present embodiment is different from the assistance processing unit 116 of the first embodiment in that a supplementary data output unit 131 is provided. In this case, the comparison determination unit 120 outputs surplus data to the difference information output unit 121 as in the first embodiment described above, and outputs information regarding missing data to the supplementary data output unit 131.

Based on the information regarding the missing data output from the comparison determination unit 120, the supplementary data output unit 131 outputs the default data of the default data list 132 to the program control unit 112 and the difference information output unit 121 as supplementary data to supplement the missing data. The program control unit 112 executes the diagnostic assistance program 101 by using data, which is obtained by adding the supplementary data to the medical data of the designated data range, as input data. The difference information output unit 121 outputs the information of surplus data and the information of supplementary data, instead of the information of missing data, to the screen generation unit 113 as difference information.

The default data list 132 is stored in the storage device 30A in advance. As shown in FIG. 21, default data for each item of the medical data is registered in the default data list 132. The default data is data that can be applied in common to a plurality of patients. For example, items of dosing are a standard dose and a standard dosing period that are set for each drug, items of vital signs are average blood pressure, normal temperature, or average pulse of an adult, and items of test substance examinations are average examination values. The supplementary data output unit 131 reads default data, which matches the items of missing data, from the default data list 132, and outputs the read default data as supplementary data.

Figure 22:
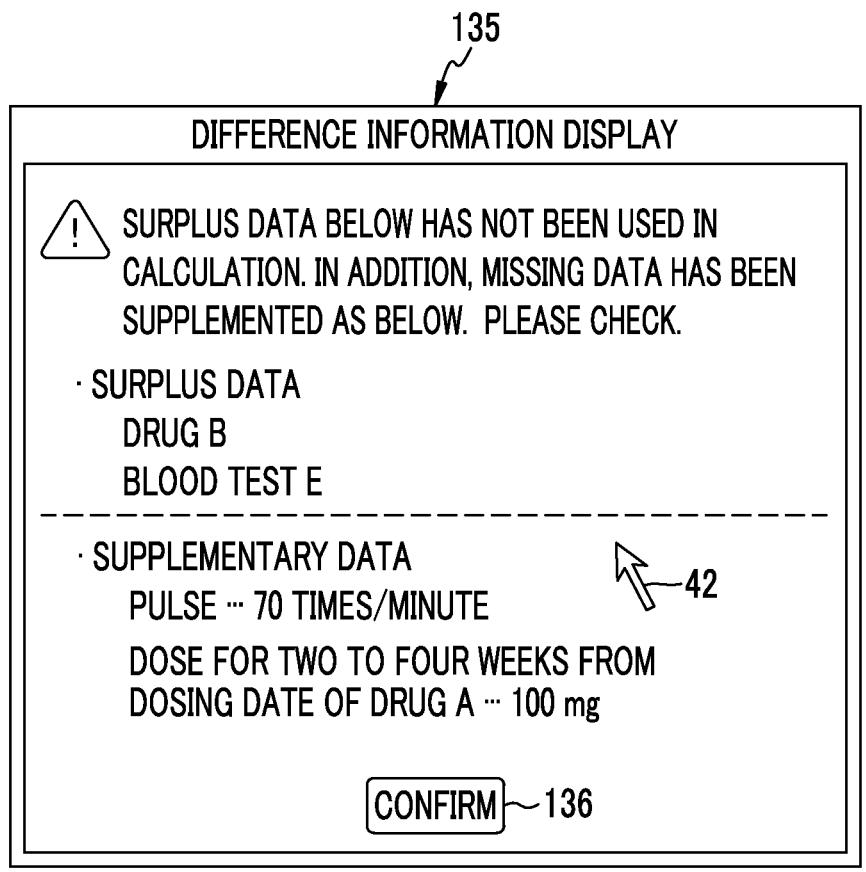
FIG. 22 is a diagram showing a difference information display screen to display supplementary data.

When supplementary data is transmitted as difference information from the difference information output unit 121, the screen generation unit 113 generates a difference information display screen 135 shown in FIG. 22.

In FIG. 22, the same message as in the difference information display screen 95 shown in FIG. 14, which shows that there is surplus data and the surplus data has not been used for the execution of the diagnostic assistance program 101, and a message showing that there is missing data and the missing data has been supplemented with supplementary data are displayed on the difference information display screen 135. In addition, the specific content of the supplementary data is displayed. In FIG. 22, "70 times/minute" is illustrated as supplementary data of "pulse", and "100 mg" is illustrated as supplementary data of "dose of two to four weeks from the dosing date of drug A". In addition, a confirm button 136 is a button for removing the display of the difference information display screen 135, similar to the confirm button 96 of the difference information display screen 95 shown in FIG. 14.

According to the present embodiment, since the missing data is supplemented with supplementary data if there is missing data, diagnostic assistance information that is reliable to some extent can be output based on the diagnostic assistance program 101. Therefore, it is possible to reduce a possibility of the calculation of the diagnostic assistance program 101 becoming useless due to the output of the significantly unreliable diagnostic assistance information. In addition, since the information of supplementary data is output as difference information and this is displayed on the difference information display screen 135, it is possible to notify the doctor that the diagnostic assistance information is not reliable, and it is possible to notify the doctor of which kind of data has been used as supplementary data, as in the first embodiment described above. If the doctor determines that the value of the displayed supplementary data is not so different from the value of the patient who is currently examined, it is possible to determine that there is no influence on the reliability of the diagnostic assistance information and make a diagnosis based on the diagnostic assistance information. If the doctor determines that the value of the supplementary data is greatly different from the value of the patient, it is possible to designate a range again and to output the diagnostic assistance information again by the execution of the diagnostic assistance program 101.

In addition, default data may be registered for each of small classifications, such as patient attributes including the sex, age, body type, residential area, and nationality of the patient and diseases which the patient suffers from. For example, "36.5° C." is registered as the default data of body temperature of an adult, and "37.0° C." that is slightly higher than "36.5° C." is registered as the default data of body temperature of an infant. In this manner, it is possible to further improve the reliability of the diagnostic assistance information when there is missing data.

Third Embodiment

Instead of the default data, estimated data that is estimated for each patient based on the medical data may be used as supplementary data.

Figure 23:
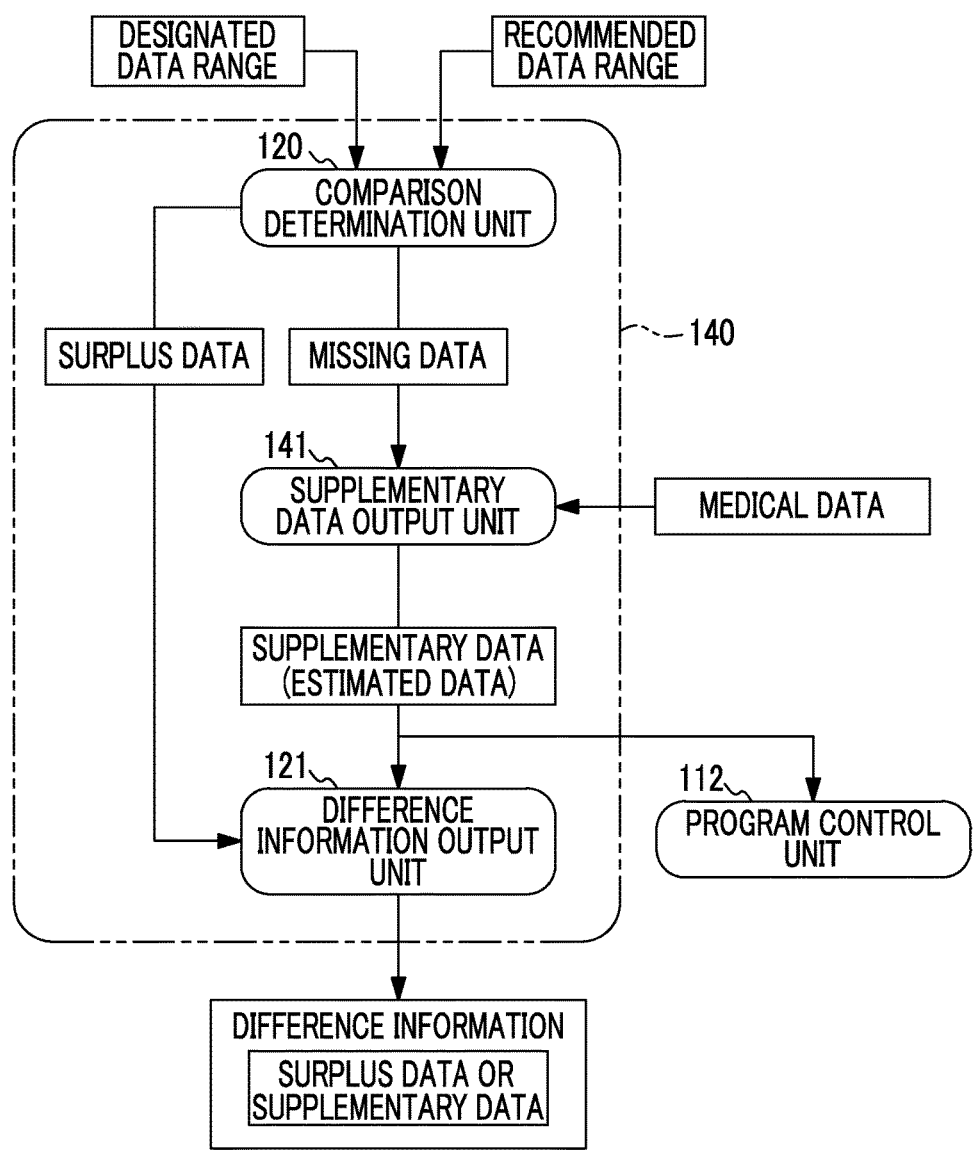
FIG. 23 is a block diagram showing the detailed configuration of an assistance processing unit including a supplementary data output unit in a third embodiment.

In FIG. 23, a supplementary data output unit 141 of an assistance processing unit 140 built in the CPU of the medical assistance server of the present embodiment receives information regarding the missing data from the comparison determination unit 120, and receives the medical data in the entire course of treatment for the patient from the medical data acquisition unit 111. The supplementary data output unit 141 estimates missing data from the medical data, and outputs the estimated data to the program control unit 112 and the difference information output unit 121 as supplementary data. As in the second embodiment described above, the program control unit 112 executes the diagnostic assistance program 101 by using the medical data of the designated data range and the supplementary data as input data. The difference information output unit 121 outputs the information of surplus data and the information of supplementary data, as difference information, to the screen generation unit 113.

If the missing data is, for example, measured values of vital signs or examination values of test substance examinations, the supplementary data output unit 141 extracts measured values of vital signs or examination values of test substance examinations in a certain period from the medical data, calculates the average value, and sets the average value as estimated data. Thus, also by using the estimated data as supplementary data, the same effect as in the second embodiment described above is obtained. In addition, since the estimated data is estimated from the medical data of a target patient unlike default data, it is possible to further improve the reliability of the diagnostic assistance information when there is missing data. In addition, since it is not necessary to store the default data, it is possible to reduce the capacity load of the storage device 30A.

The present embodiment and the second embodiment may be combined. In this case, estimated data may be used as missing data that can be estimated from other medical data, and default data may be used as missing data that cannot be estimated.

When there is data corresponding to data that is required for the execution of a diagnostic assistance program but is missing (missing data) in the medical data in the entire course of treatment for the patient, which is acquired in response to the acquisition request and is stored in the storage device 30A, it is preferable to extract medical data corresponding to the missing data and set the medical data as supplementary data. In addition, only when there is no data corresponding to the missing data in the entire course of treatment for the patient, default data or estimated data may be set as supplementary data.

Although one computer that forms the medical assistance server 11 is made to operate as a medical assistance device in each of the embodiments described above, a plurality of computers may have the respective functions of the medical assistance device in a distributed manner. For example, in order to improve the processing capacity or reliability, the medical assistance server 11 may be formed by a plurality of server computers that are separated from each other as hardware. Specifically, the medical assistance server 11 is formed by two server computers, that is, a server computer including the request receiving unit 110, the medical data acquisition unit 111, and the program control unit 112 and a server computer including the screen generation unit 113, the screen output control unit 114, the recommended data range acquisition unit 115, and the assistance processing unit 116. Alternatively, the client terminal 12 may be made to have some or all of the functions of the request receiving unit 110 and the like. Thus, the hardware configuration of a computer can be appropriately changed according to the required performance, such as processing capacity, safety, or reliability.

Needless to say, in order to ensure the safety or reliability, an application program, such as the operation program 100, may be duplicated or may be stored in a plurality of storage devices in a distributed manner, without being limited to hardware.

Fourth Embodiment

Figure 24:
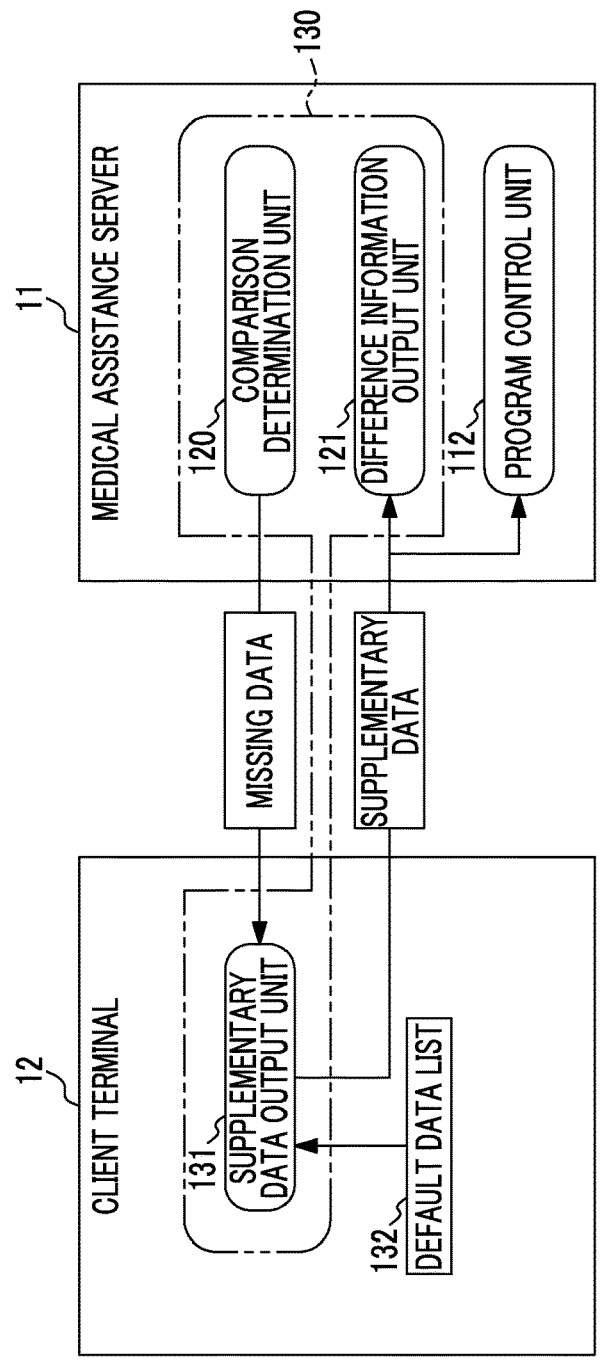
FIG. 24 is a block diagram showing the configuration in which a supplementary data output unit is provided in a client terminal in a fourth embodiment.

FIG. 24 shows an example in which the supplementary data output unit 131 of the second embodiment is provided in the client terminal 12. In this case, the assistance processing unit 130 is built by the medical assistance server 11 and the client terminal 12. The default data list 132 is stored in the storage device 30B (not shown) of the client terminal 12.

The comparison determination unit 120 outputs information regarding missing data to the communication unit 33A of the medical assistance server 11. As a result, the information regarding missing data is transmitted from the communication unit 33A to the client terminal 12. The supplementary data output unit 131 outputs supplementary data to the communication unit 33B of the client terminal 12. As a result, the supplementary data is transmitted to the medical assistance server 11. The supplementary data is transmitted to the program control unit 112 and the difference information output unit 121 in the medical assistance server 11. Subsequent processing is the same as in the second embodiment described above. In addition, the supplementary data output unit 141 of the third embodiment may be provided in the client terminal 12.

Fifth Embodiment

Figure 25:
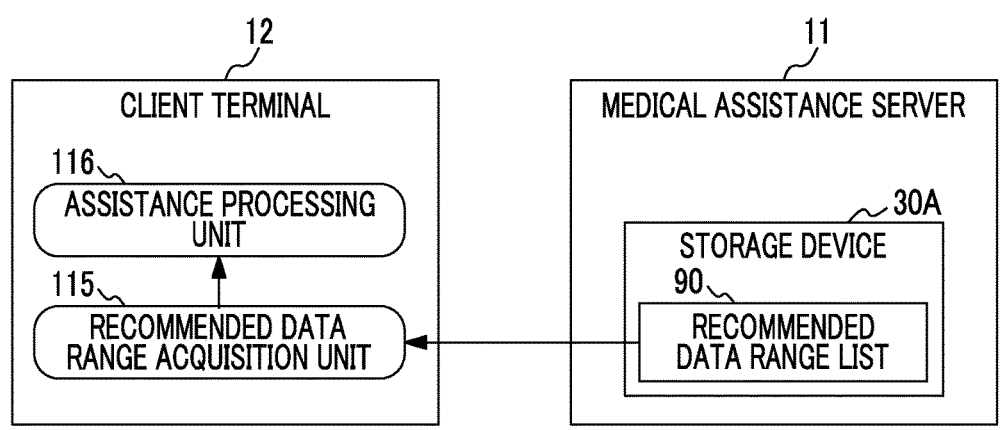
FIG. 25 is a block diagram showing the configuration in which a recommended data range acquisition unit is provided in a client terminal in a fifth embodiment.

FIG. 25 shows an example in which the recommended data range acquisition unit 115 and the assistance processing unit 116 are provided in the client terminal 12. Although not shown, the screen generation unit 113 and the screen output control unit 114 are also provided in the client terminal 12. In this case, the client terminal 12 asks the medical assistance server 11 about the recommended data range corresponding to the diagnostic assistance program 101 that the doctor has selected as a program to be used. The medical assistance server 11 transmits the recommended data range from the recommended data range list 90 stored in the storage device 30A to the client terminal 12 through the communication unit 33A. The recommended data range acquisition unit 115 acquires the recommended data range received by the communication unit 33B of the client terminal 12. Thus, the recommended data range acquisition unit 115 may read the recommended data range from the recommended data range list 90 in the built-in storage device 30 as in the first embodiment described above, or may receive the recommended data range from the external storage device 30 as in the present embodiment.

When the client terminal 12 has a function of a medical assistance device, the request receiving unit 110 receives the same request as the distribution request or the display switching request in the first embodiment described above by the operation instruction from the input device 35B through the operation screen displayed on the display 34B of the client terminal 12. The screen output control unit 114 outputs various operation screens including the medical data display screen 15 to the display 34B of the client terminal 12.

Although the medical assistance system 10 constructed in the medical facility is illustrated and the medical assistance server 11 is used in one medical facility in each of the embodiments described above, the medical assistance server 11 may be used in a plurality of medical facilities.

In each of the embodiments described above, the medical assistance server 11 is communicably connected to the client terminal 12 installed in one medical facility through the network 14, such as a LAN, and provides application services called medical assistance in response to the request from the client terminal 12. In order to make the medical assistance server 11 available in a plurality of medical facilities, the medical assistance server 11 is communicably connected to each client terminal 12 installed in the plurality of medical facilities, for example, through a wide area network (WAN), such as the Internet or a public communication network. Then, the medical assistance server 11 receives requests from the client terminals 12 in the plurality of medical facilities through the WAN, and provides application services for medical assistance to the client terminals 12. When using a WAN it is preferable to build a virtual private network (VPN) or to use a communication protocol with a high security level, such as hypertext transfer protocol secure (HTTPS), in consideration of information security. In this case, the installation location and management entity of the medical assistance server 11 may be a data center managed by a company that is different from the medical facilities, or may be one of the plurality of medical facilities, for example.

In each of the embodiments described above, both the range of each item determined by item designation, such as the designated data item and the recommended data item, and a period determined by the designation of a temporal range, such as the designated data period and the recommended data period, are illustrated as a range to be used for the input data that is input to the diagnostic assistance program 101. However, at least one of the range of the item and the period may be used.

In the first embodiment described above, the medical data display screen 15 also serves as a screen for designating the designated data range. However, it is also possible to generate the screen for designating the designated data range separately from the medical data display screen 15. In the first embodiment described above, a patient ID is input on the startup screen, and a disease is selected on the medical data display screen 15 shown in FIG. 6. However, the input of a patient ID and the selection of a disease may be performed on one screen.

In addition, medical data in the entire course of treatment for the patient is displayed on the medical data display screen 15 shown in FIG. 6, diagnostic assistance program 101 and medical data corresponding to the display items set in the disease-specific list 80 are displayed on the medical data display screen 15 shown in FIG. 7, and display items and the diagnostic assistance program 101 are narrowed down by the selection of the disease. However, such narrowing down may not be performed. In this case, the check box 76, the period designating bar 77, the radio button 78, and the calculation execution button 79 of the medical data display screen 15 shown in FIG. 7 are provided in the medical data display screen 15 shown in FIG. 6, so that the medical data display screen 15 shown in FIG. 6 functions as a screen for designating the designated data range. In the various information display region 54, the names of all diagnostic assistance programs 101 that can be used in the medical assistance server 11 are listed. However, considering that the number of diagnostic assistance programs 101 will increase in the future, narrowing down the display items or the available diagnostic assistance programs 101 for each disease as in the first embodiment is preferable because it becomes easy to designate an item or to select the diagnostic assistance program 101.

Alternatively, the check box 76 and the period designating bar 77 of the medical data display screen 15 shown in FIG. 7 may be provided in the medical data display screen 15 shown in FIG. 6, so that the doctor selects a disease after designating the designated data range. When the number of diagnostic assistance programs 101 corresponding to a disease is one, the selection of the disease becomes the selection of the diagnostic assistance program 101. In this case, if a disease is selected, the diagnostic assistance program 101 is automatically started without waiting for the selection of the calculation execution button 79. Therefore, it is possible to reduce the time and effort of selecting the calculation execution button 79. In this case, if the doctor does not require diagnostic assistance information, the doctor may select a disease without designating a designated data range, and may designate the designated data range only when the diagnostic assistance information is required. That is, in the normal work flow in which a doctor views the medical data display screen 15 and performs diagnosis based on the content, an unnecessary operation or display is not performed when the diagnostic assistance information is not required, and the diagnostic assistance program 101 can be executed only when the diagnostic assistance information is required.

Without being limited to the disease, when the medical assistance server 11 for each patient or each medical department, such as surgery, internal medicine, pediatrics, and ophthalmology, is used in a plurality of medical facilities, display items and the diagnostic assistance program 101 may be set according to the medical unit, such as a medical facility, an event (for example, admission and discharge dates or surgery date), a medical phase that is a progressive stage (for example, examination stages such as a first visit, an image examination, and a test substance examination, or progression of cancer or diabetes) of treatment or disease, or a medical purpose such as the malignancy determination of a tumor, reduction effect determination, side effects determination of drugs, and size measurement of a lesion. If the display items and the diagnostic assistance program 101 are set in a multiple manner for each disease and each medical department, it is possible to further narrow down the display items and the diagnostic assistance program 101. Therefore, it becomes easier to designate an item and to select the diagnostic assistance program 101.

In the first embodiment described above, candidates for the diagnostic assistance program 101 to be used are displayed on the medical data display screen 15 shown in FIG. 7 after the selection of a disease, and the selection of the diagnostic assistance program 101 to be used and the designation of a range are received. However, the invention is not limited thereto. For example, the medical data display screen 15 shown in FIG. 10 may be displayed by executing one typical diagnostic assistance program 101 automatically with the medical data of the recommended data range as input data after the selection of a disease, and then the designation of a range may be received. The typical diagnostic assistance program 101 is registered in advance in the disease-specific list 80. In this case, if the doctor is satisfied with diagnostic assistance information according to the typical diagnostic assistance program 101, an unnecessary operation, such as the designation of a range or the selection of the diagnostic assistance program 101, is not required. If the doctor is not satisfied with diagnostic assistance information according to the typical diagnostic assistance program 101, it is possible to receive the designation of a range.

In addition, the diagnostic assistance program 101 is not always used but is used in a limited case, such as when a doctor performs difficult determination. Therefore, it is not user-friendly to make a doctor select the diagnostic assistance program 101 each time. For this reason, first, the typical diagnostic assistance program 101 is automatically executed to display the diagnostic assistance information, so that the doctor designates a range by selecting the diagnostic assistance program 101 only when the diagnostic assistance information is required and the doctor continues treatment by neglecting the diagnostic assistance information when the diagnostic assistance information is not required. In this manner, the screen operation becomes simple, and is not cumbersome.

Thus, cases of the selection of the diagnostic assistance program 101 to be used include a case in which the candidate for the diagnostic assistance program 101 is directly selected as in the first embodiment described above and a case in which the diagnostic assistance program 101 to be used is indirectly selected by selecting a different option (for example, a disease) from the diagnostic assistance program 101. In addition, options different from the diagnostic assistance program 101 may be other medical units, such as a patient, medical department, medical facility, event, medical phase, and medical purpose, without being limited to the disease.

As the diagnostic assistance program 101 to be used, only one diagnostic assistance program 101 may be selectable as in the first embodiment described above, or a plurality of diagnostic assistance programs 101 may be selectable. When a plurality of diagnostic assistance programs 101 are selectable, a range is designated for each of the selected diagnostic assistance program 101.

As an examination image to be distributed as medical data from the image server 22 to the medical assistance server 11, the entire examination image may be selected, or a partial region of the examination image, for example, a region of interest surrounding the lesion reflected in the examination image, may be selected.

In the first embodiment described above, even if there is missing data, calculation based on the diagnostic assistance program 101 is performed using only the medical data of the designated data range as input data. However, when there is missing data, it is also possible to simply display the difference information without executing the diagnostic assistance program 101. Unless the difference information is displayed, the doctor has no way to know that their range designation is wrong. Therefore, also in this case, it is meaningful to display the difference information.

In each of the embodiments described above, the information of surplus data, missing data, or supplementary data is output as difference information. However, information indicating that there is a difference between the designated data range and the recommended data range may be simply output as difference information. In this case, a warning message showing that there is a difference between the designated data range and the recommended data range is displayed on the difference information display screen in order to attract the attention of the doctor. As means for notifying the doctor that there is a difference between the designated data range and the recommended data range, sound (for example, "read a message" or beeping sound) or vibration may be output in addition to or instead of the difference information display screen. In short, it is preferable to be able to notify the doctor that there is a difference between the designated data range and the recommended data range.

In each of the embodiments described above, not only the diagnostic assistance information but also the difference information is displayed. However, difference information may be displayed before executing the diagnostic assistance program 101 so that the doctor selects whether to continue the calculation.

In the first embodiment described above, the recommended data range is defined as the range of input data for outputting the reliable diagnostic assistance information. However, the recommended data range is not limited to the range of input data for outputting the reliable diagnostic assistance information, and it is also possible to provide a margin to some extent. For example, the recommended data range may be configured to include an essential data range that is essential as a range to be used for input data and an allowable data range that is not essential as a range to be used for input data but is allowed. In this case, it is preferable to display the essential data range and the allowable data range so as to be distinguishable on the difference information display screen. Then, it can be seen that the reliability of the diagnostic assistance information is particularly low if there is missing data in the essential data range and that there is no serious problem in the reliability of the diagnostic assistance information if there is missing data in the allowable data range.

Not only the diagnostic assistance information of the target patient whose patient ID has been input on the startup screen but also the diagnostic assistance information of other patients who have the same disease and have similar symptoms may be output. In this case, in addition to the request for acquisition of medical data of the target patient, the medical data acquisition unit 111 outputs a request for acquisition of medical data of a patient having measurement values of vital signs or examination values of test substance examinations similar to those of the target patient or a patient having a lesion size and a lesion type similar to that of the target patient, for example. The program control unit 112 outputs diagnostic assistance information based on not only the medical data of the target patient but also the medical data of other patients. Thus, by outputting not only the diagnostic assistance information of the target patient but also the diagnostic assistance information of other patients who have the same disease and have similar symptoms, it is possible to perform diagnosis in a shorter time.

When medical units including a disease or a medical purpose are selected as in the pull-down menu 55 for selecting the disease in the first embodiment and the display is switched on the medical data display screen having the check box 76, such as the medical data display screen 15 shown in FIG. 7, a check mark may be put in advance in the check boxes 76 of items that are common in the medical unit. The items that are common in the medical unit are items common to the recommended data items of a plurality of diagnostic assistance programs 101 when there is a plurality of diagnostic assistance programs 101 corresponding to a certain disease, for example. Such common items are registered in advance for each medical unit, and a check mark is put in the check boxes 76 of the common items when the screen generation unit 113 generates the medical data display screen 15 and then the medical data display screen 15 is transmitted to the screen output control unit 114. In this manner, since some items are already selected from the beginning, it is possible to improve work efficiency when a doctor edits items to be designated by adding or removing an item as necessary. When there is only one diagnostic assistance program 101 corresponding to the medical unit, a check mark is put in the check box 76 of the item used in the one diagnostic assistance program 101 in advance. Therefore, since a doctor does not have to do editing, work efficiency is good.

The form of holding the recommended data range is not limited to the list form in which the recommended data ranges of the respective diagnostic assistance programs 101 are collected, such as the recommended data range list 90 shown in the first embodiment, and each diagnostic assistance program 101 may hold the recommended data range.

It is needless to say that the invention is not limited to the above embodiments and various configurations can be adopted without departing from the scope of the invention. In addition, it is also possible to appropriately combine the above-described various embodiments or various modifications. In addition to the program, the invention also extends to a storage medium for storing the program.

What is claimed is:

1. A medical assistance device, comprising:
   a storage device, configured to store historical medical data of a patient, a plurality of diagnostic assistance programs, and recommended data ranges preset for each of the diagnostic assistance programs;
   a processor, configured to:
   control a diagnostic assistance program, selected from among the plurality of diagnostic assistance programs, that is executed to perform calculation using medical data of the patient as input data and output a result of the calculation as diagnostic assistance information for assisting diagnosis of the patient, wherein the medical data of the patient is extracted from the historical medical data of the patient;
   receive an input of a designated data range, which is designated as a range to be used for the input data, of the medical data, wherein the input of the designated data range is input by a medical staff other than the patient;
   acquire a recommended data range, from the stored recommended data ranges, that is preset for the selected diagnostic assistance program and is recommended as a range to be used for the input data, of the medical data of the patient; and
   in response to determining a difference between the designated data range and the recommended data range display difference information indicating the difference on a graphical user interface configured to display the diagnostic assistance information.

2. The medical assistance device according to claim 1, wherein, in a case where surplus data that is data outside the recommended data range and inside the designated data range is present, the processor is configured to output the surplus data as the difference information.

3. The medical assistance device according to claim 2, wherein the processor is configured to execute the diagnostic assistance program using only the medical data of the recommended data range as the input data in a case where there is the surplus data.

4. The medical assistance device according to claim 1, wherein, in a case where missing data that is data outside the designated data range and inside the recommended data range is present, the processor is configured to output information regarding the missing data as the difference information.

5. The medical assistance device according to claim 4, wherein the processor is configured to execute the diagnostic assistance program using only the medical data of the designated data range as the input data in a case where there is the missing data.

6. The medical assistance device according to claim 4, wherein the processor is further configured to output supplementary data to supplement the missing data, wherein the processor is configured to execute the diagnostic assistance program using data, which is obtained by adding the supplementary data to the medical data of the designated data range, as the input data.

7. The medical assistance device according to claim 6, wherein the processor is configured to output the supplementary data as the difference information.

8. The medical assistance device according to claim 6, wherein the supplementary data is default data that is set in advance and is applicable in common to a plurality of the patients.

9. The medical assistance device according to claim 6, wherein the supplementary data is estimated data that is estimated for each patient based on the medical data.

10. The medical assistance device according to claim 1, wherein the medical data includes a plurality of items, and at least one of the plurality of items is recorded in time series, and
the designated data range is at least one of a range of the item determined by designation of the item and a period determined by designation of a temporal range.

11. The medical assistance device according to claim 1, wherein the processor is further configured to generate a medical data display screen to display the medical data.

12. The medical assistance device according to claim 11, wherein the medical data display screen has a function of designating the designated data range, and
the processor is configured to receive the designated data range that is designated through the medical data display screen.

13. The medical assistance device according to claim 11, wherein the difference information is displayed on the medical data display screen.

14. The medical assistance device according to claim 11, wherein the diagnostic assistance information is displayed on the medical data display screen.

15. The medical assistance device according to claim 11, wherein the medical data display screen is a screen that is common to the diagnostic assistance programs.

16. The medical assistance device according to claim 1, wherein the diagnostic assistance program used for each medical unit is registered in advance, and
the processor is configured to execute the diagnostic assistance program corresponding to the medical unit.

17. The medical assistance device according to claim 16, wherein the medical unit is at least one of the patient, a disease which the patient suffers from, a department, a medical facility, an event that occurs in a course of treatment for the patient, a medical phase that is a progressive stage of treatment or disease, and a medical purpose.

18. A medical assistance system, comprising:
a medical assistance server;
a client terminal; and
a network that communicably connects the medical assistance server and the client terminal to each other,
wherein the medical assistance server functions as the medical assistance device according to claim 1.

19. The medical assistance system according to claim 18, wherein, in a case where missing data that is data outside the designated data range and inside the recommended data range is present, the medical assistance server outputs supplementary data to supplement the missing data,
wherein the medical assistance server executes the diagnostic assistance program using data, which is obtained by adding the supplementary data to the medical data of the designated data range, as the input data.

20. The medical assistance system according to claim 18, wherein, in a case where missing data that is data outside the designated data range and inside the recommended data range is present, the medical assistance server transmits information regarding the missing data to the client terminal, and the client terminal outputs supplementary data to supplement the missing data and transmits the supplementary data to the medical assistance server, and
wherein the medical assistance server executes the diagnostic assistance program using data, which is obtained by adding the supplementary data to the medical data of the designated data range, as the input data.

21. The medical assistance system according to claim 18, wherein the medical assistance server reads the recommended data range from the storage device thereof.

22. The medical assistance system according to claim 18, wherein the client terminal receives the recommended data range that is transmitted from the medical assistance server.

23. The medical assistance device according to claim 1, wherein the processor is configured to display a screen listing the plurality of diagnostic assistance programs to be selected and set a selected diagnostic assistance program among the plurality of diagnostic assistance programs as the diagnostic assistance program to output the diagnostic assistance information.

24. An operation method of a medical assistance device, comprising:
controlling a diagnostic assistance program, selected from among a plurality of diagnostic assistance programs stored in the medical assistance device with recommended data ranges preset for each of the diagnostic assistance programs, that is executed to perform calculation using medical data of a patient as input data and output a result of the calculation as diagnostic assistance information for assisting diagnosis of the patient, wherein historical medical data of the patient is stored in the medical assistance device, and wherein the medical data of the patient is extracted from the historical medical data of the patient;
receiving an input of a designated data range, which is designated as a range to be used for the input data, of the medical data, wherein the input of the designated data range is input by a medical staff other than the patient;
acquiring a recommended data range, from the stored recommended data ranges, that is preset for the selected diagnostic assistance program and is recommended as a range to be used for the input data, of the medical data of the patient; and in response to determining a difference between the designated data range and the recommended data range, displaying difference information indicating the difference on a graphical user interface configured to display the diagnostic assistance information.

25. A non-transitory computer-readable recording medium on which an operation program for a medical assistance device is recorded, wherein the program causes the medical assistance device to:

control a diagnostic assistance program, selected from among a plurality of diagnostic assistance programs stored in the medical assistance device with recommended data ranges preset for each of the diagnostic assistance programs, that is executed to perform calculation using medical data of a patient as input data and output a result of the calculation as diagnostic assistance information for assisting diagnosis of the patient, wherein historical medical data of the patient is stored in the medical assistance device, and wherein the medical data of the patient is extracted from the historical medical data of the patient;

receive an input of a designated data range, which is designated as a range to be used for the input data, of the medical data, wherein the input of the designated data range is input by a medical staff other than the patient;

acquire a recommended data range, from the stored recommended data ranges, that is preset for the selected diagnostic assistance program and is recommended as a range to be used for the input data, of the medical data of the patient; and in response to determining a difference between the designated data range and the recommended data range display difference information indicating the difference on a graphical user interface configured to display the diagnostic assistance information.

* * * * *